United States Patent
Li

(10) Patent No.: US 9,878,052 B2
(45) Date of Patent: Jan. 30, 2018

(54) COMPOUNDS FOR TARGETED IMMUNOTHERAPY

(71) Applicant: Shanghai Birdie Biotech, Inc., Beijing (CN)

(72) Inventor: Lixin Li, Beijing (CN)

(73) Assignee: BIRDIE BIOPHARMACEUTICALS INC., Grand Cayman (KY)

( * ) Notice: Subject to any disclaimer, the term of this patent is extended or adjusted under 35 U.S.C. 154(b) by 0 days.

(21) Appl. No.: 14/408,268

(22) PCT Filed: Jul. 16, 2013

(86) PCT No.: PCT/CN2013/079441
§ 371 (c)(1),
(2) Date: Dec. 15, 2014

(87) PCT Pub. No.: WO2014/012479
PCT Pub. Date: Jan. 23, 2014

(65) Prior Publication Data
US 2015/0174268 A1    Jun. 25, 2015

(30) Foreign Application Priority Data

Jul. 18, 2012 (CN) .......................... 2012 1 0248481

(51) Int. Cl.
| | |
|---|---|
| *C12P 21/08* | (2006.01) |
| *C07K 16/00* | (2006.01) |
| *A61K 47/48* | (2006.01) |
| *A61K 39/39* | (2006.01) |
| *A61K 31/4745* | (2006.01) |
| *A61K 45/06* | (2006.01) |
| *A61K 47/68* | (2017.01) |

(52) U.S. Cl.
CPC .... *A61K 47/48384* (2013.01); *A61K 31/4745* (2013.01); *A61K 39/39* (2013.01); *A61K 45/06* (2013.01); *A61K 47/6803* (2017.08); *A61K 47/6849* (2017.08); *A61K 47/6855* (2017.08)

(58) Field of Classification Search
None
See application file for complete search history.

(56) References Cited

U.S. PATENT DOCUMENTS

| | | | |
|---|---|---|---|
| 5,389,640 A | 2/1995 | Gerster et al. | |
| 8,067,546 B2 | 11/2011 | McDonagh et al. | |
| 8,337,856 B2 * | 12/2012 | Blattler | A01K 67/0271 424/130.1 |
| 8,383,768 B2 * | 2/2013 | Singh | A61K 9/107 424/185.1 |
| 8,663,643 B2 * | 3/2014 | Berry | A61K 31/337 424/178.1 |
| 8,951,528 B2 | 2/2015 | Stoermer et al. | |
| 9,259,459 B2 | 2/2016 | Keler et al. | |
| 9,522,958 B2 | 12/2016 | Epstein et al. | |
| 2003/0139364 A1 | 7/2003 | Krieg et al. | |
| 2005/0180983 A1 | 8/2005 | Keler et al. | |
| 2005/0239735 A1 | 10/2005 | Miller et al. | |
| 2006/0135459 A1 | 6/2006 | Epstein et al. | |
| 2006/0142202 A1 | 6/2006 | Alkan et al. | |
| 2006/0188913 A1 | 8/2006 | Krieg et al. | |
| 2008/0031887 A1 | 2/2008 | Lustgarten | |
| 2009/0004194 A1 | 1/2009 | Kedl | |
| 2009/0123467 A1 | 5/2009 | Atul et al. | |
| 2012/0039916 A1 | 2/2012 | Zurawski et al. | |
| 2012/0231023 A1 | 9/2012 | Zurawski et al. | |
| 2015/0141625 A1 | 5/2015 | Stoermer et al. | |
| 2016/0324983 A1 | 11/2016 | Li | |
| 2016/0375148 A1 | 12/2016 | Li | |
| 2017/0028079 A1 | 2/2017 | Li | |
| 2017/0056391 A1 | 3/2017 | Li | |
| 2017/0114137 A1 | 4/2017 | Li | |

FOREIGN PATENT DOCUMENTS

| | | |
|---|---|---|
| WO | 2001/000244 A2 | 1/2001 |
| WO | 2004/029206 | 4/2004 |
| WO | 2004/062603 | 7/2004 |
| WO | 2006/020266 | 2/2005 |
| WO | 2006/071997 A2 | 7/2006 |
| WO | 2006/091720 | 8/2006 |
| WO | 2007/030642 A2 | 3/2007 |
| WO | 2007103048 A2 | 9/2007 |
| WO | 2008/052187 A2 | 5/2008 |
| WO | 2008/079924 A1 | 7/2008 |
| WO | 2008/097870 | 8/2008 |
| WO | 2008/115319 A2 | 9/2008 |
| WO | 2009/018500 | 2/2009 |

(Continued)

OTHER PUBLICATIONS

Sousa, CRE, 2004. Current Opin in Immunol. 16:21-25.*
Hurvitz et al. 2012. Therap. Adv. In Med Onc. 4:235-245.*
Smyth et al. 2005. Mol. Immunol. 42:501-510.*
Mosser et al. 2008. Nat Rev. Immunol. 8:958-969.*
Blencowe et al. 2010. Polym Chem 2011. 2:773-790.*
Betting, D.J. et al., In vivo eradication of a rituximab-resistant human CD20+ B cell lymphoma by rituximabCpG oligodeoxynucleotide conjugate is mediated by natural akiller cells and complement, Blood, 2009, vol. 114, No. 22, p. 302, ISSN 0064971.
Bonifaz, L. et al., Efficient targeting of protein antigen to the dendritic cell receptor DEC-205 in the steady site leads to antigen presentation on majot histocompatibility complex class I products and peripheral CD8+ T cell tolerance, The Jornal of Experimental Medicine, vol. 196, No. 12, Dec. 16, 2002, pp. 1627-1638, XP002983189.

(Continued)

*Primary Examiner* — Shulamith H Shafer
(74) *Attorney, Agent, or Firm* — K&L Gates LLP; Louis C. Cullman; David Diamond

(57) ABSTRACT

Compounds for targeted immunotherapy, compositions comprising the compounds and use of the compounds in the treatment of diseases such as cancer are disclosed. The compounds having the structure of formula TM-Ln-AM, wherein TM is a targeting moiety, AM is an activating moiety that is capable of activating a human dendritic cell, NK cell, or tumor cell, or a combination thereof, Ln is a linker, and n is an integer selected from 0 and 1.

9 Claims, 11 Drawing Sheets

(56) References Cited

FOREIGN PATENT DOCUMENTS

| WO | 2009/093250 | | 7/2009 |
|---|---|---|---|
| WO | 2013/166110 | A1 | 11/2013 |
| WO | 2014/012479 | A1 | 1/2014 |
| WO | 2014/022758 | A1 | 2/2014 |
| WO | 2014/032021 | A1 | 2/2014 |
| WO | 2015/103987 | A1 | 7/2015 |
| WO | 2015/103989 | A1 | 7/2015 |
| WO | 2015/103990 | A1 | 7/2015 |
| WO | 2016/004875 | A1 | 1/2016 |
| WO | 2016/004876 | A1 | 1/2016 |
| WO | 2016/034085 | A1 | 3/2016 |

OTHER PUBLICATIONS

Carter, Robert W., et al., "Preferential induction of CD4+ T cell responses through in vivo targeting of antigen to dendritic cell-associated C-type lectin-1", The Journal of Immunology, vol. 177, No. 4, Aug. 15, 2006, pp. 2276-2284, XP002503158.
Melani, Cecilia et al., "Targeting of Interleukin 2 to human ovarian carcinoma by fusion with a single-chain Fv of antifolate receptor antibody", Cancer Research, vol. 58, No. 18, Sep. 15, 1998, pp. 4146-4154, XP002421527.
Timmerman, J., et al., In vivo activity of rituximab 0-CpG oligodeoxynucleotide conjugate against rituximab-resistant human CD20+ B-cell lymphoma, Journal of Clinical Oncology, 2009, vol. 27, No. 15, p. 8529, ISSN 0732183X.
Singaporean Search Report and Written Opinion for Singaporean Patent Application No. 11201500399S filed on Jul. 16, 2013 (Search completed on Mar. 16, 2016 and dated Apr. 12, 2016).
Supplementary European Search Report for European Patent Application No. 13820359.1 filed on Jul. 16, 2013 (Search completed on Jan. 27, 2016 and dated Apr. 1, 2016).
Supplementary Partial European Search Report for European Patent Application No. 13820359.1 filed on Jul. 16, 2013 (Search completed on Jan. 27, 2016 and dated Feb. 3, 2016).
International Search Report and Written Opinion for International Application No. PCT/CN2015/083583 filed on Jul. 8, 2015.
International Search Report and Written Opinion for International Application No. PCT/CN2015/083585 filed on Jul. 8, 2015.
International Search Report and Written Opinion for International Application No. PCT/CN2015/070377 filed on Jan. 8, 2015.
International Search Report and Written Opinion for International Application No. PCT/CN2015/070380 filed on Jan. 8, 2015.
International Search Report and Written Opinion for International Application No. PCT/CN2015/070379 filed on Jan. 8, 2015.
International Search Report and Written Opinion for International Application No. PCT/CN2015/088456 filed on Aug. 29, 2015.
Suzanne et al., Targeting the PD-1/B7-H1(PD-L1) pathway to activate anti-tumor immunity. Current Opinion in Immunology, vol. 24, No. 2, pp. 207-212 (2012).
U.S. Appl. No. 15/346,553, filed Nov. 8, 2016.
U.S. Appl. No. 15/110,679, filed Jul. 8, 2016.
U.S. Appl. No. 15/110,690, filed Jul. 8, 2016.
U.S. Appl. No. 15/508,033, filed Mar. 1, 2017.
Engel et al., The pharmacokinetics of Toll-like receptor agonists and the impact on the immune system. Expert Rev. Clin. Pharmacol., 4(2):275-289 (2011).
Lu et al., TLR agonists for cancer immunotherapy: tipping the balance between the immune stimulatory and inhibitory effects. Front. Immunol., vol. 5, pp. 1-4 (2014).
Sznol et al., Antagonist antibodies to PD-1 and B7-H1 (PD-L1) in the treatment of advanced human cancer. Clin. Cancer Res., 19(5): 1021-1034 (2013).
Topalian et al., Targeting the PD-1/B7-H1(PD-L1) pathway to activate anti-tumor immunity. Curr. Opin. Immunol., 24(2):207-212 (2012).
West, Anthony. Solid State Chemistry and its Applications. Wiley, New York, 358 (1988).

\* cited by examiner

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: VEGFR peptide

<400> SEQUENCE: 1

Ala Thr Trp Leu Pro Pro Arg
1               5

<210> SEQ ID NO 2
<211> LENGTH: 10
<212> TYPE: PRT
<213> ORGANISM: Artificial Sequence
<220> FEATURE:
<223> OTHER INFORMATION: Artificial cyclic targeting moiety

<400> SEQUENCE: 2

Cys Asp Cys Arg Gly Asp Cys Phe Cys Gly
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Artificial cyclic targeting moiety

<400> SEQUENCE: 3

Asn Cys Asn Gly Arg Cys
1               5

<210> SEQ ID NO 4
<211> LENGTH: 10
<212> TYPE: PRT
<213> ORGANISM: Artificial Sequence
<220> FEATURE:
<223> OTHER INFORMATION: Artificial targeting moiety

<400> SEQUENCE: 4

Cys Thr Thr His Trp Gly Phe Thr Leu Cys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Lyp-1 targeting moiety

<400> SEQUENCE: 5

Cys Gly Asn Lys Arg Thr Arg Gly Cys
1               5
```

COMPOUNDS FOR TARGETED IMMUNOTHERAPY

CROSS REFERENCE TO RELATED APPLICATIONS

This application claims the benefit of, and priority to, Chinese Patent Application Serial No. 201210248481.9, filed on Jul. 18, 2012, the entire disclosure of which is hereby incorporated by reference in its entirety.

FIELD OF THE INVENTION

The present invention relates to compounds for targeted immunotherapy, as well as compositions comprising the same. Further, the present invention relates to the use of the compounds in the treatment of diseases such as cancer.

BACKGROUND OF THE INVENTION

Therapeutic antibodies have been used in clinical applications for over twenty years. Currently, there are fifteen anti-tumor antibody drugs in clinic, including Rituxan (1997), Herceptin (1998), Mylotarg (2000), Campath (2001), Zevalin (2002), Bexxer (2003), Avastin (2004), Erbitux (2004), Vectibix (2006); Arzerra (2009); Benlysta (2011); Yervoy (2011); Adcetris (2011); Perjeta (2012); and Kadcyla (2013). These antibodies target mainly four molecules: EGFR, Her2, CD20 and VEGF.

In general, therapeutic antibodies kill tumor cells via three mechanisms (Scott A M, Wolchok J D, Old L J. Antibody therapy of cancer. Nat Rev Cancer. (2012), 12:278-87): (1) Direct antibody action, that is, blockade or agonist activity of ligand/receptor signaling, induction of apoptosis, and delivery of drugs or cytotoxic agents. Antibody receptor activation activity can produce direct tumor cell killing effect. For example, some antibodies can bind to receptors on the surface of tumor cells, activate the receptor, leading to apoptosis (e.g., in mitochondria). Antibodies can also mediate tumor cell killing by receptor-antagonistic activity. For example, certain antibodies can bind to cell surface receptors and block dimerization, kinase activation and downstream signaling, thereby inhibiting proliferation and promote apoptosis. Binding of antibodies to an enzyme can lead to neutralization, signal abrogation, and cell death. (2) Through immune-mediated cell killing mechanisms include complement-dependent cytotoxicity (CDC), antibody-dependent cell-mediated cytotoxicity (ADCC), T cell function regulation, etc. Immune-mediated killing of tumor cells can be accomplished through the following ways: induction of phagocytosis, complement activation, antibody-dependent cell-mediated cytotoxicity, genetically modified T cells being targeted to the tumor by single-chain variable fragment (scFv), through antibody-mediated antigenic cross presentation to dendritic cell to activate T cells, inhibition of T cell inhibitory receptors, such as cytotoxic T lymphocyte-associated antigen 4 (CTLA4). Of them, the Fc portion of the antibody feature is especially important for CDC and ADCC-mediated tumor cell killing effect. (3) Specific effect of antibody on tumor vasculature and matrix, through trapping of vascular receptor antagonist or ligand to induce vascular and stromal cells ablation, including: stromal cell inhibition, delivery of toxins to stromal cells, and delivery of toxins to the vasculature. (Scott A M, Wolchok J D, Old L J. Antibody therapy of cancer. Nat Rev Cancer. 2012, 12 (4):278-87).

Therapeutic monoclonal antibody drugs have advanced anti-cancer drug research and development. However, some issues still need further study to be solved, such as antibody immunogenicity, tolerance of long-term use of tumor target, and long-term effects of simple single blockade of signal transduction pathway. In short, a simple majority of antibodies are difficult to achieve long-term efficient inhibition and killing of tumor cells.

In 1964, "Nature" magazine presented the new idea of antibody-drug conjugates (ADC) technology, which in recent years have seen breakthroughs. ADC covalently links antibody with a highly toxic drug (toxin) through a chemical linker (linker). Antibody recognizes cancer cell surface antigen molecule, the endocytosis ADC brings it into cytoplasm, and in particular intracellular environment toxins released after hydrolysis of the linker kills cells.

Seattle Genetics has developed such drug Brentuximab Vedotin (trade name Adcetris) that has been approved by the FDA to market. It is monomethyl auristatin E (MMAE), a synthetic toxic anti-cancer drug, coupled with antibody targeting lymphoma cells specific CD30 molecule, with improved efficacy of killing tumor cells.

Currently, there are dozens of such ADC drugs in clinical trials. Among them, Genentech and Immunogen jointly developed trastuzumab coupled with maytansines as a drug named ado-trastuzumab emtansine (Kadcyla), also known as T-DM1, to treat breast cancer. In February 2013, the FDA has approved T-DM1 for human epidermal growth factor receptor 2 (Her2)-positive metastatic breast cancer. Maytansines is a small molecule toxin that can bind tubulin and prevent formation of microtubules by forming non-reducing dual-maleimide-propanediol complex. Trastuzumab acts on breast cancer and gastric cancer by targeting human Her2. It was approved for Her2-positive cancer. However, trastuzumab cannot promote apoptosis of all of the Her2 positive cells. T-DM1 combines the selective targeting Her2 receptor trastuzumab with the potent cytotoxic agent maytansine to kill tumor cells. T-DM1 antibody binds Her2 receptors, causing cellular internalization of the maytansines released from conjugates, thereby killing the tumor cells. T-DM1 has better overall efficacy and pharmacokinetic properties and low toxicity.

Traditional small molecule chemotherapeutic drugs have strong toxicity and pharmacokinetic advantages, but in the process of treatment of tumors may affect other physiological targets with serious side effects. Antibody-drug conjugates combines targeting function and small molecule drug with particular pharmacokinetics. The structure of antibody-drug conjugates is the attachment of a monoclonal antibody with targeting function to a compound with specific pharmacological properties. This technique requires the therapeutic antibody have binding specificity to a target, to be coupled to a molecule with therapeutic effect or other functions such as cyto-toxins. Many factors affect the effect of this type of antibodies, such as endocytosis of the coupled antibody, stability of the coupling, and release and killing activity of the toxins.

Toxin molecules currently being used include tubulin inhibitors Auristatin analogues monomethyl auristatin E, monomethyl auristatin F and maytansine. Monomethyl auristatin E is a synthetic microtubule polymer inhibitor that can inhibit microtubule aggregation, interfere tumor cell mitosis and induce apoptosis (Naumovski L and Junutula J R. Glembatumumab vedotin, a conjugate of an anti-glycoprotein non-metastatic melanoma protein B mAb and monomethyl auristatin E for treatment of melanoma and breast cancer. Curr Opin Mol Ther 2003; 12 (2): 248-57.

Francisco J A, Cerveny C G et al. cAC10-vcMMAE, an anti-CD30-monomethyl auristatin E conjugate with potent and selective antitumor activity. Blood 102 (4): 1458-65. Monomethyl auristatin F is an anti-mitotic Auristatin derivative with a charged phenylalanine residue at C terminus. In comparison to uncharged MMAE it minimizes damage to cell signaling pathway and minimizes cytotoxicity. A large number of test with CD30 cells found that mAb-maleimidocaproyl-valine-citrulline-p-aminobenzyloxycarbonyl-MMAF (mAb-L1-MMAF) has a toxicity that is 2,200 times stronger than MMAF only (Doronina S O et al., Enhanced activity of monomethylauristatin F through monoclonal antibody delivery: effects of linker technology on efficacy and toxicity. Bioconjug Chem, 2006; 17 (1): p 114-24). Maytansine is an antimitotic agent acting as an inhibitor of tubulin polymerization, thus interfering with formation of microtubules in the cell nucleus. Maytansine also inhibits DNA, RNA, and protein synthesis, with the greatest effect being seen on DNA synthesis.

Antibodies-drug conjugates have direct and indirect anticancer effect. The antibody blocks or activates ligand/receptor signaling, induces apoptosis, and at the same time can present or deliver payload drug directly or indirectly (such as a drug, toxin, small interfering RNA or radioisotope) to the tumor cells. Therapeutic antibody drug conjugate utilizes dual characteristics of the antibody and the coupled drug, first is the binding function that it specifically binds to the target molecule, second is the tumor cell killing function of the antibody itself, and the third is the particular effect of the conjugated drug. Current antibody-drug conjugates drugs are limited in how to kill tumor cells directly. However, because of the tough requirement of technologies in antibody, linker molecule, toxin molecules, and conjugation, as well as the limitation of bringing toxins within the tumor microenvironment molecules, there are still some difficulties in actual clinical studies.

SUMMARY OF THE INVENTION

In one aspect, the present invention provides a compound having the structure of Formula (I):

TM-L$n$-AM        (I), wherein TM is a targeting moiety, AM is an activating moiety that is capable of activating human immune cells, including but not limited to dendritic cells, macrophages, monocytes, myeloid-derived suppressor cells, NK cells, B cells, T cells or tumor cells, or a combination thereof, Ln is a linker, and n is an integer selected from 0 and 1.

In some embodiments, the human dendritic cell is a plasmacytoid dendritic cell. In some embodiments, the human dendritic cell is a myeloid dendritic cell.

In some embodiments, the AM is capable of binding specifically to human toll like receptor 7 (TLR7) and/or TLR8; or activating human immune cells via TLR7 and/or TLR8.

In another aspect, the present invention provides a compound having the structure of Formula (I):

TM-L$n$-AM        (I), wherein TM is a targeting moiety, AM is an activating moiety that is capable of binding specifically to human TLR7 and/or TLR8, or activating human immune cells via TLR7 and/or TLR8, Ln is a linker, and n is an integer selected from 0 and 1.

In some embodiments, wherein the AM is capable of binding specifically to both human TLR7 and TLR8; or activating human immune cells via TLR7 and/or TLR8.

In some embodiments, wherein when TM comprises an antibody, AM does not comprise a CpG oligonucleotide.

In some embodiments, wherein the targeting moiety is capable of binding to a tumor cell specifically or preferably in comparison to a non-tumor cell. In some embodiments, the tumor cell is of a carcinoma, a sarcoma, a lymphoma, a myeloma, or a central nervous system cancer.

In some embodiments, the targeting moiety is capable of binding to a tumor antigen specifically or preferably in comparison to a non-tumor antigen. In some embodiments, the tumor antigen is selected from the group consisting of: CD2, CD19, CD20, CD22, CD27, CD33, CD37, CD38, CD40, CD44, CD47, CD52, CD56, CD70, CD79, and CD137. In some embodiments, the tumor antigen is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin $\alpha v$, Integrin $\alpha v\beta$, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof.

In some embodiments, the targeting moiety comprises an immunoglobulin, a protein, a peptide, a small molecule, a nanoparticle, or a nucleic acid.

In some embodiments, the targeting moiety comprises an antibody, or a functional fragment thereof. In some embodiments, the antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Nivolumab, Dacetuzumab, Urelumab, MPDL3280A, Lambrolizumab, and Blinatumomab.

In some embodiments, the targeting moiety comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

In some embodiments, the targeting moiety comprises a ATWLPPR (SEQ ID NO:1) polypeptide of VEGFR, Thrombospondin-1 mimetics, CDCRGDCFCG (cyclic) (SEQ ID NO:2) polypeptide, SCH 221153 fragment, NCNGRC (cyclic) (SEQ ID NO:3) polypeptide, CTTHWGFTLC (SEQ ID NO:4) polypeptide, CGNKRTRGC (SEQ ID NO:5) polypeptide (LyP-1), Octreotide, Vapreotide, Lanreotide, C-3940 polypeptide, Decapeptyl, Lupron, Zoladex, or Cetrorelix.

In some embodiments, the targeting moiety comprises folic acid or a derivative thereof.

In some embodiments, the targeting moiety comprises extracellular domains (ECD) or soluble form of PD-1, CTLA4, BTLA, KIR, TIM3, 4-1BB, LAG3, full length of partial of a surface ligand amphiregulin, betacellulin, EGF, ephrin, epigen, epiregulin, IGF, neuregulin, TGF, TRAIL, or VEGF.

In some embodiments, the targeting moiety comprises a nanoparticle.

In some embodiments, the targeting moiety comprises an aptamer.

In some embodiments, the activating moiety comprises: (a) single-stranded RNA (ssRNA), preferably ORN02, ORN06, ssPoly(U), ssRNA40, ssRNA41, ssRNA-DR, or Poly(dT); or (b) a toll like receptor ligand (TLRL) analogs, preferably CL075, CL097, CL264, CL307, Gardiquimod, Loxoribine, Imiquimod, or Resiquimod.

In some embodiments, the linker is selected from the group consisting of a hydrazine group, a polypeptide, a disulfide group, and a thioether group.

In some embodiments, the linker is enzymatic cleavable. In some embodiments, the linker is not enzymatic cleavable.

In some embodiments, the present invention provides a pharmaceutical composition comprising a compound as provided herein, or a pharmaceutically acceptable salt thereof, and one or more pharmaceutically acceptable carriers.

In some embodiments, the pharmaceutical composition further comprises a second chemotherapeutic agent. In some embodiments, the chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

In yet another aspect, the present invention provides a method for treating a disease condition in a subject that is in need of such treatment, comprising: administering to the subject a pharmaceutical composition comprising a therapeutically effective amount of the compound provided herein or a pharmaceutically acceptable salt thereof, and a pharmaceutical acceptable carrier.

In some embodiments, the diseases condition is tumor. In some embodiments, the disease condition comprises abnormal cell proliferation. In some embodiments, the abnormal cell proliferation comprises a pre-cancerous lesion. In some embodiments, the abnormal proliferation is of cancer cells.

In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

In a further aspect, the present invention provides a compound having the structure of Formula (I):

$$TM\text{-}Ln\text{-}AM \quad (I),$$

wherein TM is a targeting moiety, AM is an activating moiety, Ln is a linker, and n is an integer selected from 0 and 1,
with the proviso that when TM comprises an antibody, AM does not comprise a CpG oligonucleotide or a therapeutic agent.

In some embodiments, the activating moiety comprises a TLR ligand, a Nod-Like Receptor ligand, a RIG-Like Receptor ligand, a CLR ligand, a CDS ligand, or a inflammasome inducers.

In some embodiments, the activating moiety comprises a ligand of one or more TLRs (toll like receptor ligand, TLRL) selected from the group consisting of: TLR2, TLR3, TLR4, TLR5, TLR7, TLR8, TLR7/TLR8, TLR9, and TLR10.

In some embodiments, the activating moiety comprises:
(i) a ligand of TLR2 selected from the group consisting of:
(a) a heat killed bacteria product, preferably HKAL, HKEB, HKHP, HKLM, HKLP, HKLR, HKMF, HKPA, HKPG, or HKSA, HKSP, and (b) a cell-wall components product, preferably LAM, LM, LPS, LTA, LTA, PGN, FSL, Pam2CSK4, Pam3CSK4, or Zymosan;

(ii) a ligand of TLR3 selected from the group consisting of: Poly (I:C) and Poly (A:U);

(iii) a ligand of TLR4 selected from the group consisting of: LPS and MPLA;

(iv) a ligand of TLR5 selected from the group consisting of: FLA and Flagellin;

(v) a ligand of TLR7/8 selected from the group consisting of: ORN02, ORN06, ssPoly(U), ssRNA40, ssRNA41, ssRNA-DR, Poly(dT), CL075, CL097, CL264, CL307, Gardiquimod, Loxoribine, Imiquimod, and Resiquimod;

(vi) a ligand of TLR9 selected from the group consisting of: ODN1585, ODN1668, ODN1826, ODN2006, ODN2007, ODN2216, ODN2336, ODN2395, and ODN M362;

(vii) a ligand of TLR10;

(viii) a ligand of nucleotide-oligomerization domain (NOD)-like selected from the group consisting of: NOD1 agonist (C12-iE-DAP, iE-DAP, Tri-DAP), NOD2 agonist (L18-MDP, MDP, M-TriLYS, M-TriLYS-D-ASN, Murabutide, N-Glycolyl-MDP), and NOD1/NOD2 agonists (M-TriDAP, PGN);

(ix) a ligand of one or more RIG-I-Like receptors (RLR) selected from the group consisting of: 5'ppp-dsRNA, Poly (dA:dT), Poly(dG:dC), and Poly (I:C);

(x) a ligand of one or more C-type lectin receptors (CLR) selected from the group consisting of: Curdlan AL, HKCA, HKSC, WGP, Zymosan, and Trehalose-6,6-dibehenate;

(xi) a ligand of one or more Cytosolic DNA Sensors (CDS) selected from the group consisting of: c-GMP, c-G-AMP, c-G-GMP, c-A-AMP, c-di-AMP, c-di-IMP, c-di-GMP, c-di-UMP, HSV-60, ISD, pCpG, Poly (dA:dT), Poly(dG:dC), Poly (dA), and VACV-70; or (xii) an inflammasome inducer selected from the group consisting of: (a) NLRP3 inflammasome protein complex, preferably alum Crystals, ATP, CPPD Crystals, Hermozoin, MSU Crystals, Nano-SiO2, Nigericin, and (b) AIM2 inflammasome protein complex, preferably Poly (dA:dT).

In some embodiments, the activating moiety comprises IMO2134, IMO205, MGN-1703, MGN-1704, Agatolimod, SD-101, QAX-935, DIMS0150, Pollinex Quattro, OM-174, Eritoran, TAK-242, NI-0101, Type I interferon, type II interferon, type III interferon, IL-12, IL-23, IL-18, IL-7 or IL-15.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A: Data represents mean tumor volumes (mean±SD). Tumor growth curves were stopped when tumors reached a size of 2000 mm$^3$. FIG. 4B: Body weight variations of the mice during and after therapy. No detectable weight loss was observed. FIG. 4C: Survival curves of treatment and control groups; substantial prolongation for mice which received Trastuzumab MC-vc-TLRL, or unconjugated Trastuzumab.

FIG. 5A: Therapeutic efficacy of Cetuximab MC-vc-TLRL in human lung cancer model. FIG. 5B: Body weight variations of the mice during and after therapy. No detectable weight loss was observed.

DETAILED DESCRIPTION OF THE INVENTION

Figure 1:
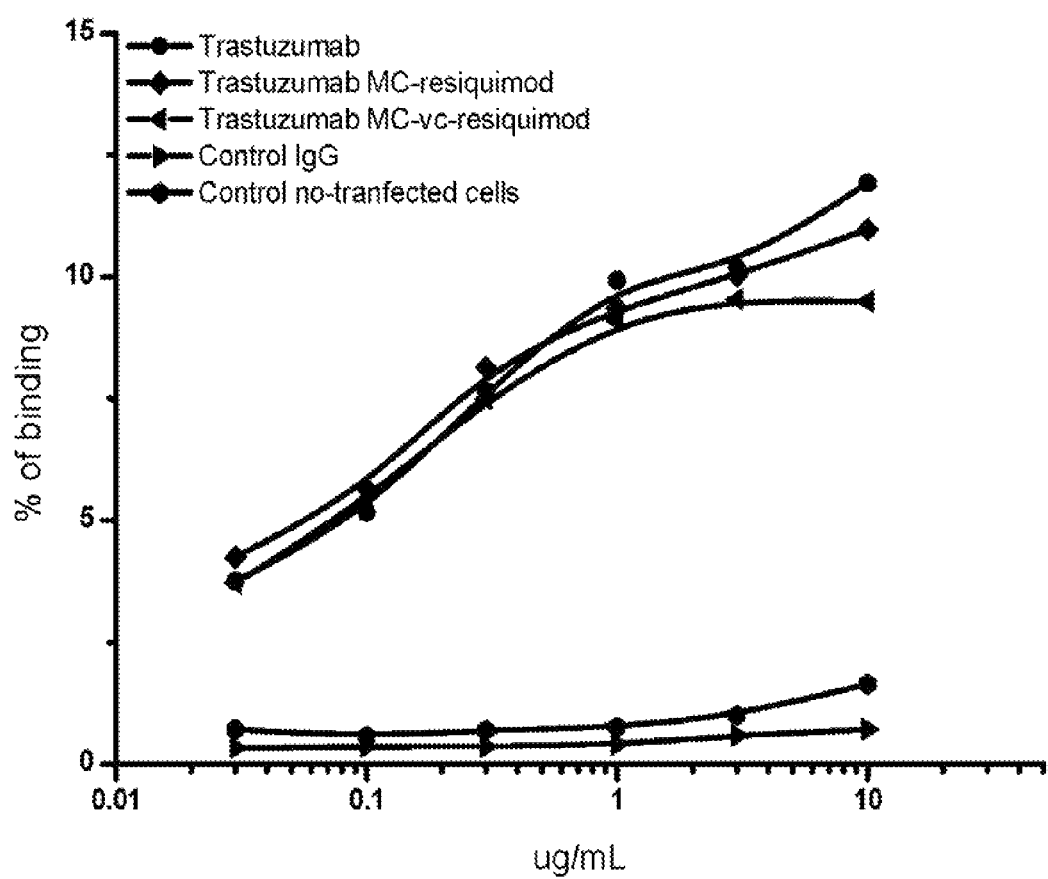
FIG. 1 depicts conjugated compound characteristics. Binding of Trastuzumab MC-vc-resiquimod and Trastuzumab-resiquimod conjugates to Her2 expressing L cells is compared with unconjugated Trastuzumab (as a reference), control human IgG, and irrelevant human IgG1 antibody, as determined by FACS analysis.
Figure 2:
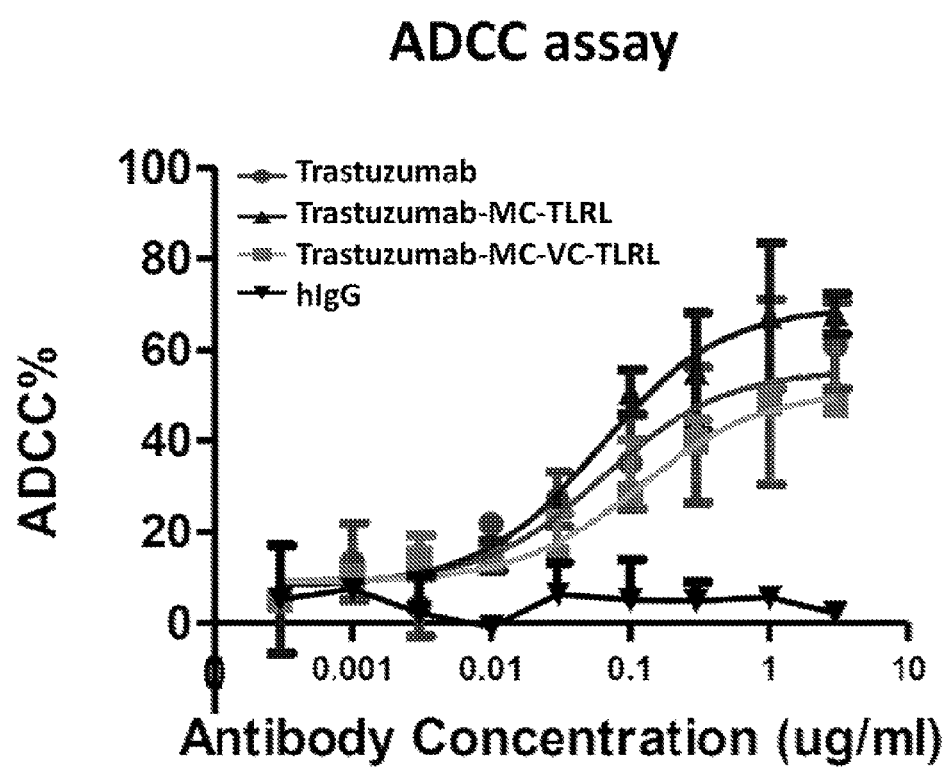
FIG. 2 depicts in vitro antibody-dependent cellular cytotoxicity (ADCC) analysis of Trastuzumab, Trastuzumab MC-vc-TLRL and Trastuzumab MC-TLRL conjugates. PBMCs (effector cells) were added with SKBR3 cells (target cells) into 96-well plates (ratio targets/effectors 1/60) for 17 h containing control human IgG1, trastuzumab, or Trastuzumab MC-vc-TLRL and Trastuzumab MC-TLRL conjugates at different concentrations. All experiments were performed in duplicate. Analysis was based on the negative SKBR3 population determination. The dead cells were stained by LDH.
Figure 3A:
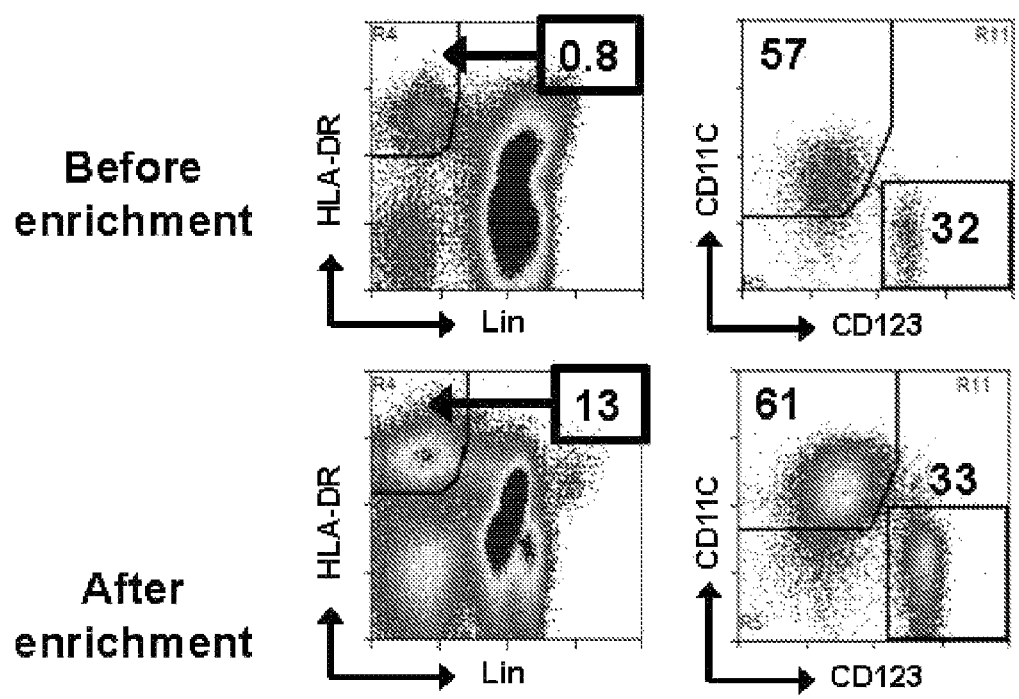
FIG. 3A depicts the percentages of DCs before and post enrichment. The numbers in upper two plots represent the percentages of DCs (HLA-DR+Lin−) of total cells before and after lineage depletion. The numbers in lower plots represent percentages of mDC (CD11C+CD123−) and pDC (CD123+CD11C−) of total DCs before and after lineage depletion.
Figure 3B:
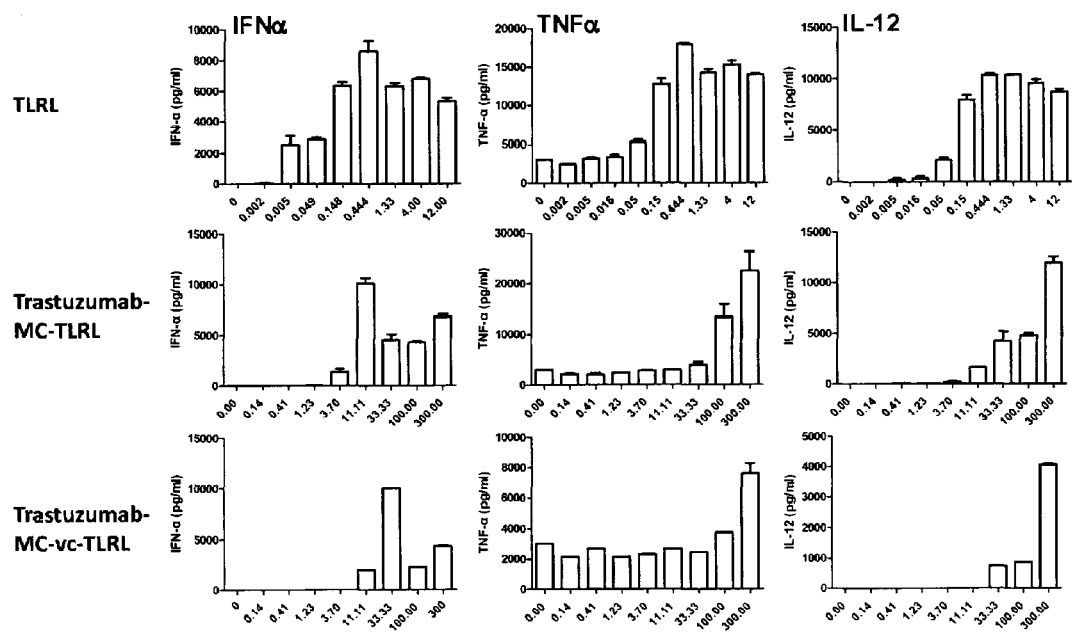
FIGS. 3B-3D depict analysis of cytokine production by purified human DCs. Purified human DCs were plated in a 96-well plate and cultured with allogeneic untreated (medium) or treated different concentration of TLRL, or Trastuzumab MC-vc-TLRL and Trastuzumab MC-TLRL directly for 20-22 h in 37'C incubator. In a separate experiment, Cetuximab MC-vc-TLRL and Cetuximab MC-TLRL in an increasing concentration were given to treat with human DCs. The supernatant were collected and human IFN-α, IL-6, IL-12(p70) and TNF-α were analyzed by ELISA. Data are given as mean±SD of triplicate cultures and are representative of independent experiments from two of three healthy donors.
Figure 3C:
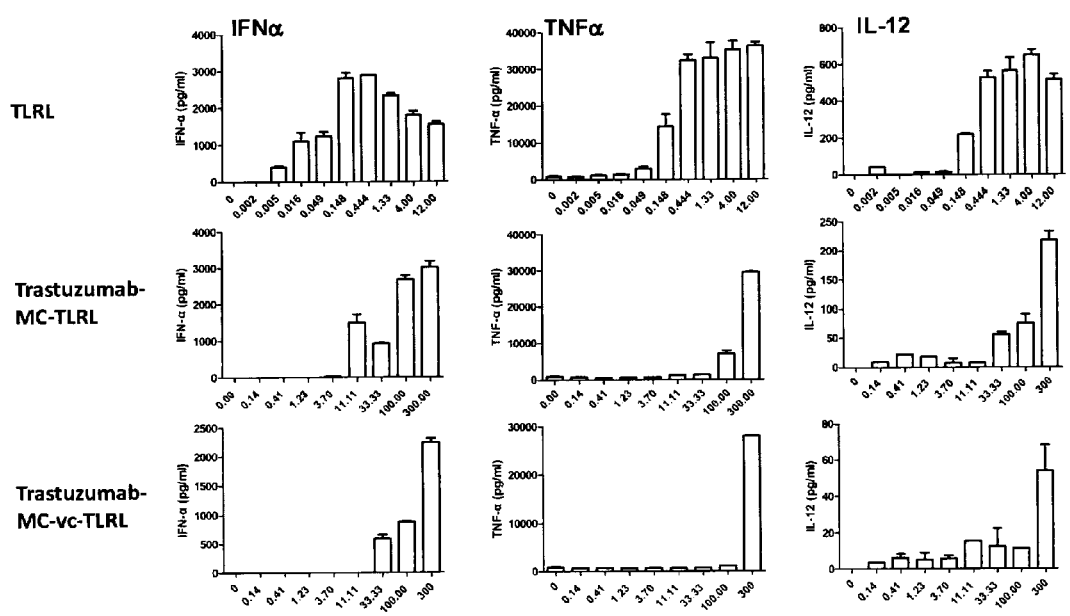
Figure 3D:
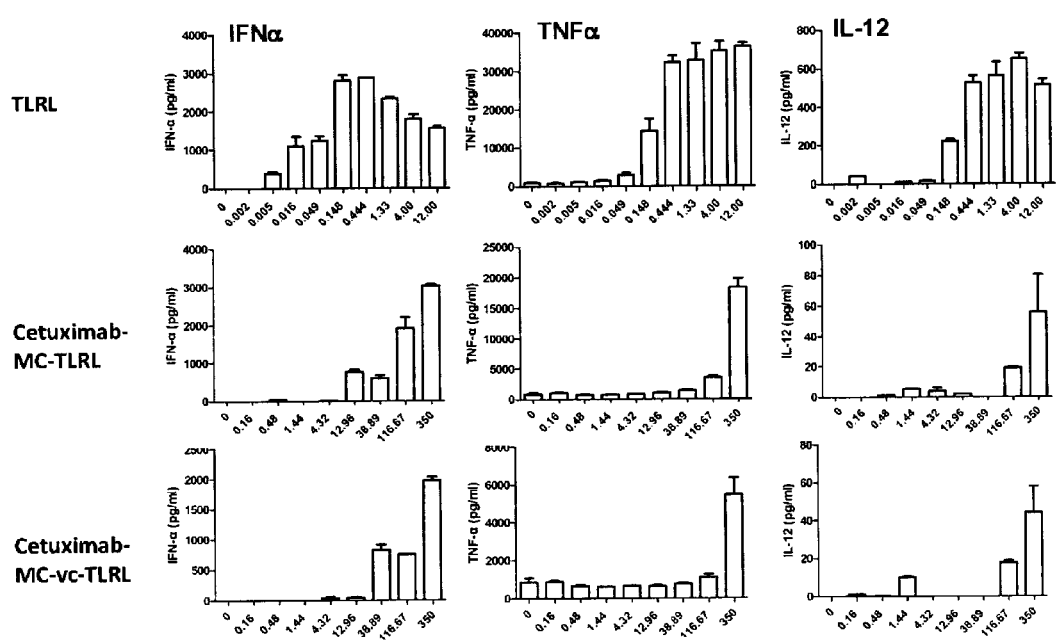
Figure 4A:
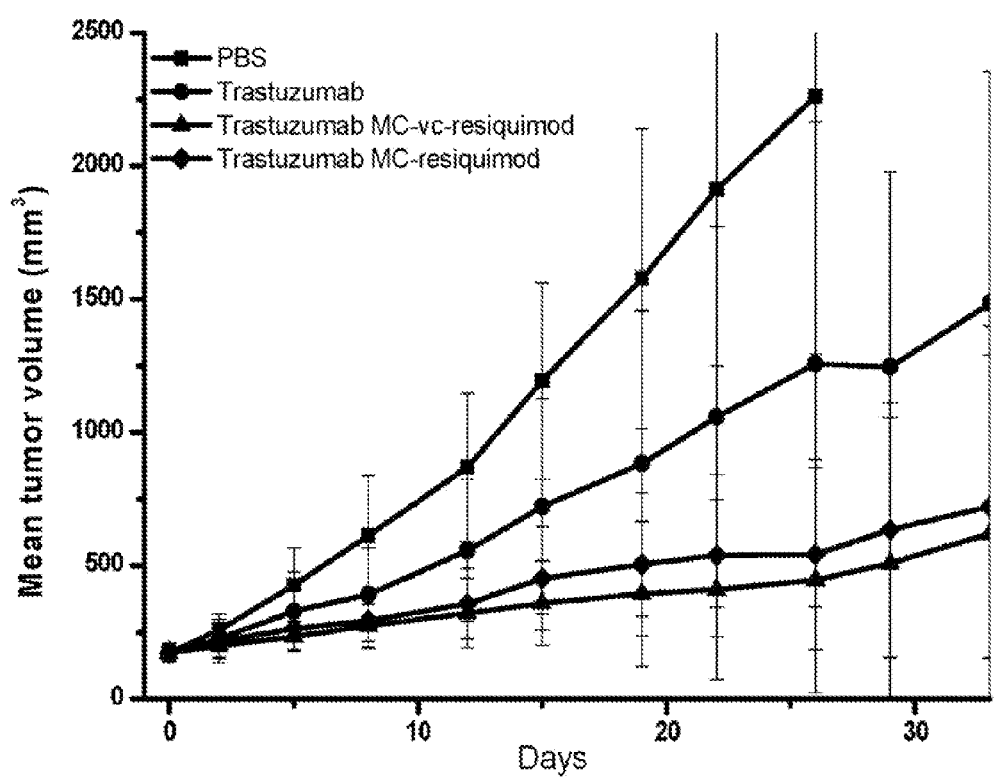
FIGS. 4A-4C depict therapeutic efficacy of Trastuzumab MC-vc-TLRL and Trastuzumab MC-TLRL in PDX gastric tumor model. BALB/c nu/nu nude mice 6-8 week-old female mice bearing subcutaneous patient derived gastric tumor were treated intravenously with 10 mg/kg of Trastuzumab MC-vc-TLRL, Trastuzumab MC-TLRL, or unconjugated Trastuzumab or saline (12 mice per group). Treatment was performed weekly for a period of 45 days. Therapy was initiated when tumors reached a size on average of 170 mm$^3$.
Figure 4B:
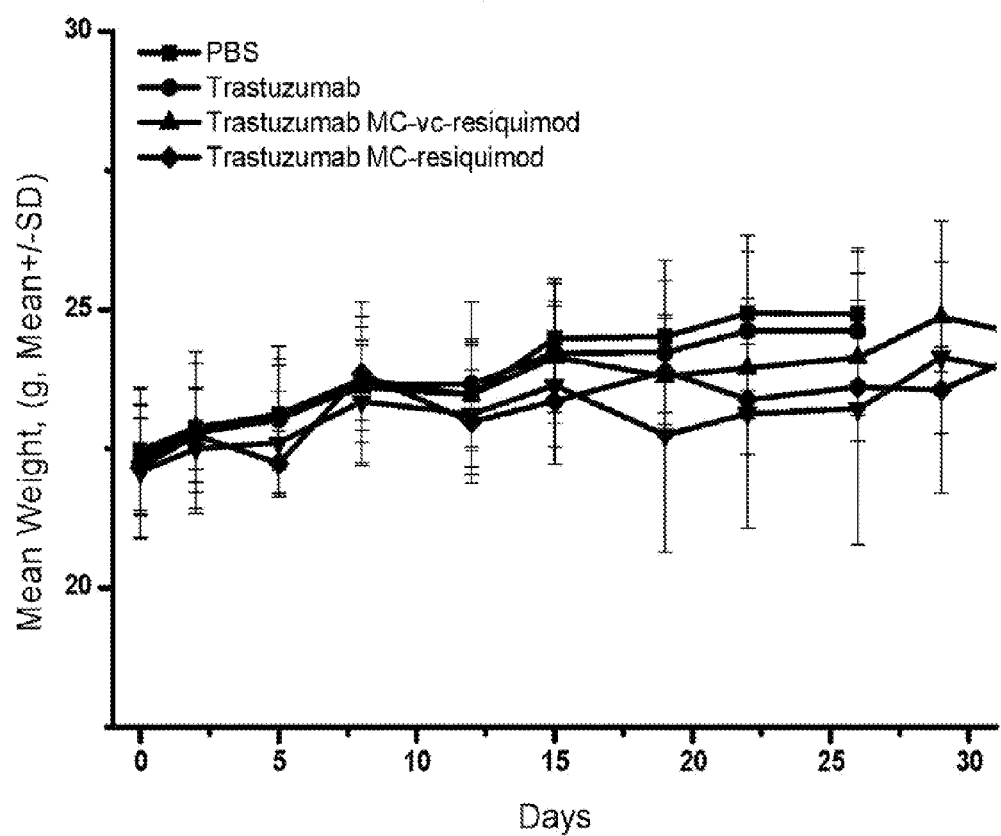
Figure 4C:
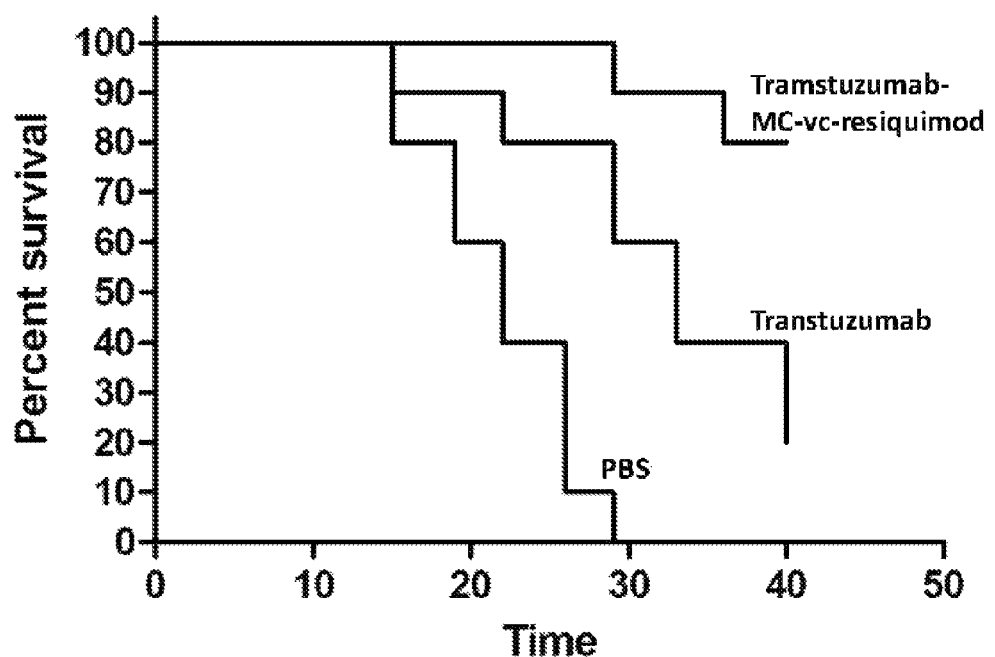
Figure 5A:
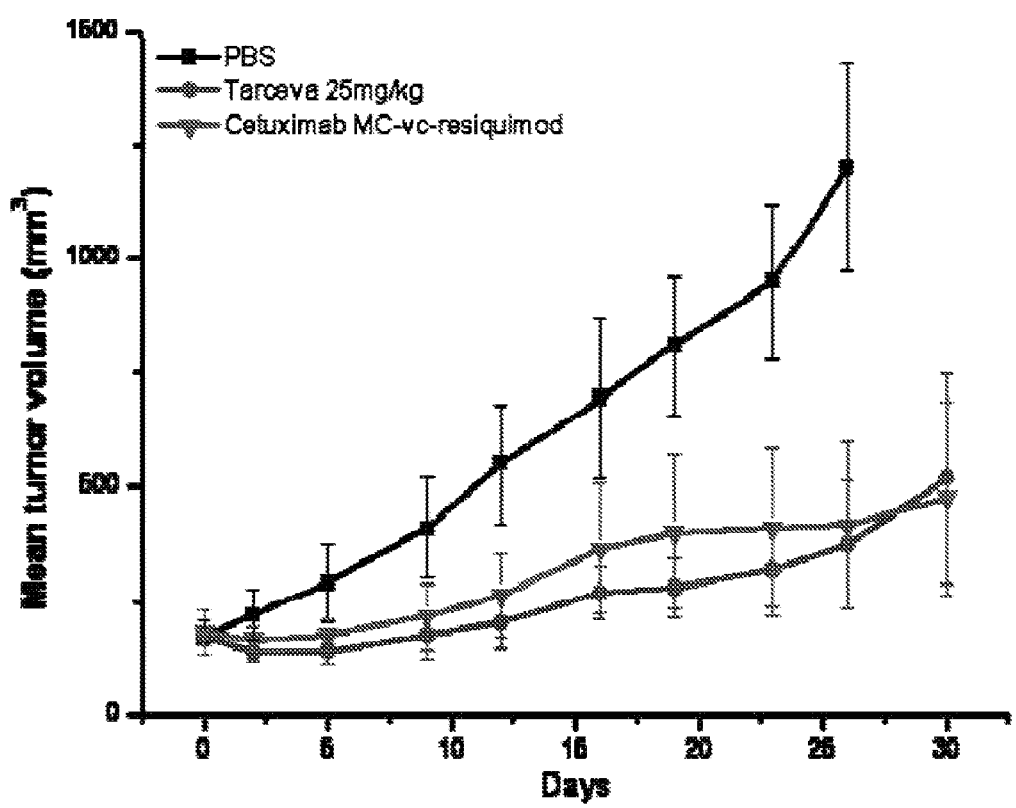
FIGS. 5A-5B depict therapeutic efficacy of Cetuximab MC-vc-TLRL in a nude/H1650 human lung cancer model. BALB/c nu/nu nude mice 6-8 week-old female mice bearing subcutaneous H1650 lung cancer cells were treated intravenously with 10 mg/kg of Cetuximab MC-vc-TLRL, or unconjugated Cetuximab or saline (12 mice per group). Treatment was performed weekly for a period of 45 days. Therapy was initiated when tumors reached a size on average of 170 mm$^3$. Data represents mean tumor volumes (mean±SD). Tumor growth curves were stopped when tumors reached a size of 2000 mm$^3$.
Figure 5B:
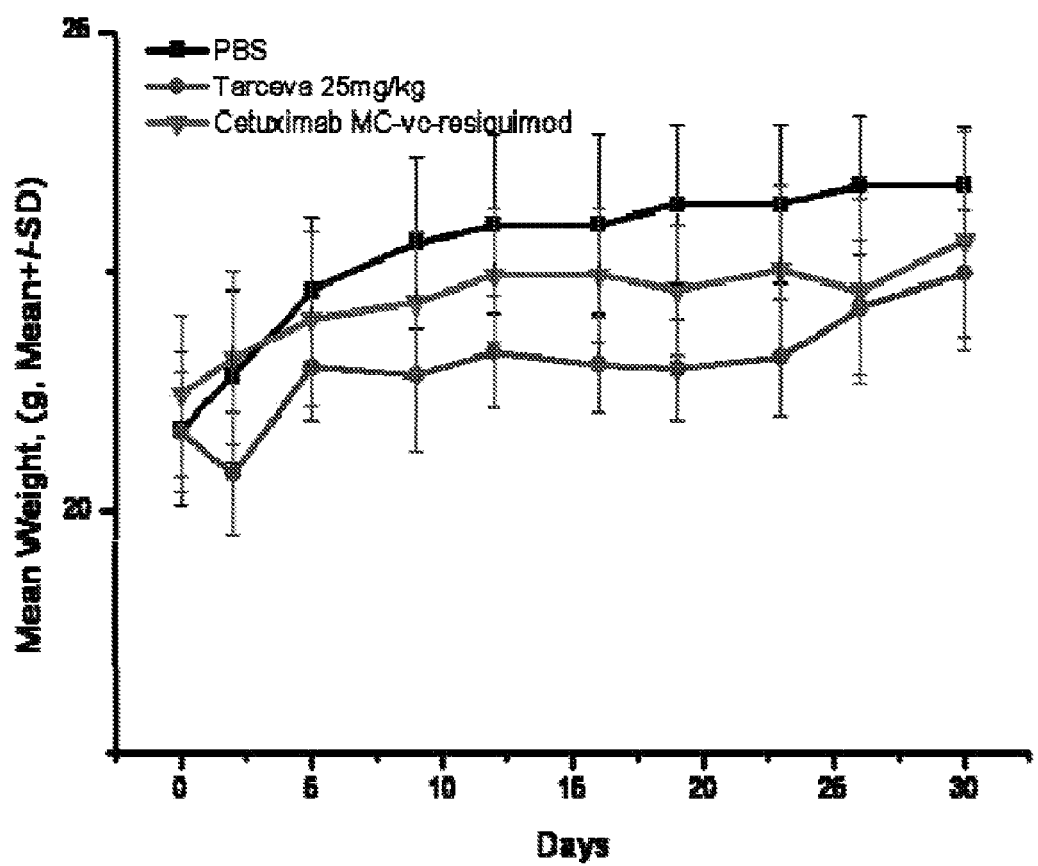

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

I. DEFINITIONS AND ABBREVIATIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well-known and commonly employed in the art. Standard techniques are used for nucleic acid and peptide synthesis. The techniques and procedures are generally performed according to conventional methods in the art and various general references, which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups, are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroakyl substituents," respectively, and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$) akyl.

As used herein, the term "heteroatom" includes oxygen (O), nitrogen (N), sulfur (S), phosphorus (P) and silicon (Si).

II. THE COMPOSITIONS

In one aspect, the present invention provides a compound having the structure of Formula (I):

TM-L$n$-AM  (I), wherein TM is a targeting moiety, AM is an activating moiety that is capable of activating a human dendritic cell, NK cell, or tumor cell, or a combination thereof, Ln is a linker, and n is an integer selected from 0 and 1.

In another aspect, the present invention provides a compound having the structure of Formula (I):

TM-L$n$-AM  (I), wherein TM is a targeting moiety, AM is an activating moiety that is capable of binding specifically to human TLR7 and/or TLR8, Ln is a linker, and n is an integer selected from 0 and 1.

In a further aspect, the present invention provides a compound having the structure of Formula (I):

TM-L$n$-AM  (I), wherein TM is a targeting moiety, AM is an activating moiety, Ln is a linker, and n is an integer selected from 0 and 1, with the proviso that when TM comprises an antibody, AM does not comprise a CpG oligonucleotide or a therapeutic agent.

A. Targeting Moiety

In general, compounds of the present invention comprise a target moiety.

By "targeting moiety (TM)" or "targeting agent" here in is meant a molecule, complex, or aggregate, that binds specifically or selectively to a target molecule, cell, particle, tissue or aggregate, which generally is referred to as a "target" or a "marker," and these are discussed in further detail herein.

In some embodiments, the targeting moiety comprises an immunoglobulin, a protein, a peptide, a small molecule, a nanoparticle, or a nucleic acid.

Exemplary targeting agents such as antibodies (e.g., chimeric, humanized and human), ligands for receptors, lecitins, and saccharides, and substrate for certain enzymes are recognized in the art and are useful without limitation in practicing the present invention. Other targeting agents include a class of compounds that do not include specific molecular recognition motifs include nanoparticles, macromolecules such as poly(ethylene glycol), polysaccharide, and polyamino acids which add molecular mass to the activating moiety. The additional molecular mass affects the pharmacokinetics of the activating moiety, e.g., serum half-life.

In some embodiments, a targeting moiety is an antibody, antibody fragment, bispecific antibody or other antibody-based molecule or compound. However, other examples of targeting moieties are known in the art and may be used, such as aptamers, avimers, receptor-binding ligands, nucleic acids, biotin-avidin binding pairs, binding peptides or proteins, etc. The terms "targeting moiety" and "binding moiety" are used synonymously herein.

Targets

By "target" or "marker" herein is meant any entity that is capable of specifically binding to a particular targeting moiety. In some embodiments, targets are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1,000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

A substance is considered to be "targeted" for the purposes described herein if it specifically binds to a nucleic acid targeting moiety. In some embodiments, a nucleic acid targeting moiety specifically binds to a target under stringent conditions. An inventive complex or compound comprising targeting moiety is considered to be "targeted" if the targeting moiety specifically binds to a target, thereby delivering the entire complex or compound composition to a specific organ, tissue, cell, extracellular matrix component, and/or intracellular compartment.

In certain embodiments, compound in accordance with the present invention comprise a targeting moiety which specifically binds to one or more targets (e.g. antigens) associated with an organ, tissue, cell, extracellular matrix component, and/or intracellular compartment. In some embodiments, compounds comprise a targeting moiety which specifically binds to targets associated with a particular organ or organ system. In some embodiments, compounds in accordance with the present invention comprise a nuclei targeting moiety which specifically binds to one or more intracellular targets (e.g. organelle, intracellular protein). In some embodiments, compounds comprise a targeting moiety which specifically binds to targets associated with diseased organs, tissues, cells, extracellular matrix components, and/or intracellular compartments. In some embodiments, compounds comprise a targeting moiety which specifically binds to targets associated with particular cell types (e.g. endothelial cells, cancer cells, malignant cells, prostate cancer cells, etc.).

In some embodiments, compounds in accordance with the present invention comprise a targeting moiety which binds to a target that is specific for one or more particular tissue types (e.g. liver tissue vs. prostate tissue). In some embodiments, compounds in accordance with the present invention comprise a targeting moiety which binds to a target that is specific for one or more particular cell types (e.g. T cells vs. B cells). In some embodiments, compounds in accordance with the present invention comprise a targeting moiety which binds to a target that is specific for one or more particular disease states (e.g. tumor cells vs. healthy cells). In some embodiments, compounds in accordance with the present invention comprise a targeting moiety which binds to a target that is specific for one or more particular developmental stages (e.g. stem cells vs. differentiated cells).

In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing cells from a plurality (e.g., 5-10 or more) of different tissues or organs in approximately equal amounts. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types.

In some embodiments, a target comprises a protein, a carbohydrate, a lipid, and/or a nucleic acid. In some embodiments, a target comprises a protein and/or characteristic portion thereof, such as a tumor-marker, integrin, cell surface receptor, transmembrane protein, intercellular protein, ion channel, membrane transporter protein, enzyme, antibody, chimeric protein, glycoprotein, etc. In some embodiments, a target comprises a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells) etc. In some embodiments, a target comprises a lipid and/or characteristic portion thereof, such as an oil, fatty acid, glyceride, hormone, steroid (e.g., cholesterol, bile acid), vitamin (e.g. vitamin E), phospholipid, sphingolipid, lipoprotein, etc. In some embodiments, a target comprises a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA.

Numerous markers are known in the art. Typical markers include cell surface proteins, e.g., receptors. Exemplary receptors include, but are not limited to, the transferrin receptor; LDL receptor; growth factor receptors such as epidermal growth factor receptor family members (e.g., EGFR, Her2, Her3, Her4) or vascular endothelial growth factor receptors, cytokine receptors, cell adhesion molecules, integrins, selectins, and CD molecules. The marker can be a molecule that is present exclusively or in higher amounts on a malignant cell, e.g., a tumor antigen.

Tumor Antigens

In some embodiments, the targeting moiety is capable of binding to a tumor cell specifically or preferably in comparison to a non-tumor cell.

The binding of target moiety to tumor cell can be measured using assays known in the art.

In some embodiments, the tumor cell is of a carcinoma, a sarcoma, a lymphoma, a myeloma, or a central nervous system cancer.

In some embodiments, the targeting moiety is capable of binding to a tumor antigen specifically or preferably in comparison to a non-tumor antigen.

By "specifically binds" or "preferably binds" herein is meant that the binding between two binding partners (e.g., between a targeting moiety and its binding partner) is selective for the two binding partners and can be discriminated from unwanted or non-specific interactions. For example, the ability of an antigen-binding moiety to bind to a specific antigenic determinant can be measured either through an enzyme-linked immunosorbent assay (ELISA) or other techniques familiar to one of skill in the art, e.g., surface plasmon resonance technique (analyzed on a BIAcore instrument) (Liljeblad et al., Glyco J 17, 323-329 (2000)), and traditional binding assays (Heeley, Endocr Res 28, 217-229 (2002)). The terms "anti-[antigen] antibody" and "an antibody that binds to [antigen]" refer to an antibody that is capable of binding the respective antigen with sufficient affinity such that the antibody is useful as a diagnostic and/or therapeutic agent in targeting the antigen. In some embodiments, the extent of binding of an anti-[antigen] antibody to an unrelated protein is less than about 10% of the binding of the antibody to the antigen as measured, e.g., by a radioimmunoassay (RIA). In some embodiments, an antibody that binds to [antigen] has a dissociation constant (KD) of <<100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). It is understood that the above definition is also applicable to antigen-binding moieties that bind to an antigen.

In certain specific embodiments, a target is a tumor marker. In some embodiments, a tumor marker is an antigen that is present in a tumor that is not present in normal organs, tissues, and/or cells. In some embodiments, a tumor marker is an antigen that is more prevalent in a tumor than in normal organs, tissues, and/or cells. In some embodiments, a tumor marker is an antigen that is more prevalent in malignant cancer cells than in normal cells.

By "tumor antigen" herein is meant an antigenic substance produced in tumor cells, i.e., it triggers an immune response in the host. Normal proteins in the body are not antigenic because of self-tolerance, a process in which self-reacting cytotoxic T lymphocytes (CTLs) and autoantibody-producing B lymphocytes are culled "centrally" in primary lymphatic tissue (BM) and "peripherally" in secondary lymphatic tissue (mostly thymus for T-cells and spleen/lymph nodes for B cells). Thus any protein that is not exposed to the immune system triggers an immune response. This may include normal proteins that are well sequestered from the immune system, proteins that are normally produced in extremely small quantities, proteins that are normally produced only in certain stages of development, or proteins whose structure is modified due to mutation.

In some embodiments, a target is preferentially expressed in tumor tissues and/or cells versus normal tissues and/or cells.

In some embodiments of the invention a marker is a tumor marker. The marker may be a polypeptide that is expressed at higher levels on dividing than on non-dividing cells. For example, Her-2/neu (also known as ErbB-2) is a member of the EGF receptor family and is expressed on the cell surface of tumors associated with breast cancer. Another example is a peptide known as F3 that is a suitable targeting agent for directing a nanoparticle to nucleolin (Porkka et al., 2002, Proc. Natl. Acad. Sci., USA, 99:7444; and Christian et al., 2003, J. Cell Biol., 163:871). It has been shown that targeted particles comprising a nanoparticle and the A10 aptamer (which specifically binds to PSMA) were able to specifically and effectively deliver docetaxel to prostate cancer tumors.

Antibodies or other drug that specifically target these tumor targets specifically interfere with and regulate signaling pathways of the biological behavior of tumor cells regulate directly, or block signaling pathway to inhibit tumor cell growth or induce apoptosis. To date, there are dozens of target drugs have been approved for solid tumors or hematological malignancies clinical research and treatment, and there are number of targeted drugs for hematological malignancies.

In some embodiments, the tumor antigen (or tumor target) is selected from the group consisting of: CD2, CD19, CD20, CD22, CD27, CD33, CD37, CD38, CD40, CD44, CD47, CD52, CD56, CD70, CD79, and CD137.

In some embodiments, the tumor antigen (or tumor target) is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y antigen, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof. The variants of the tumor antigen encompass various mutants or polypormisms known in the art and/or naturally occurred.

Antibodies

In some embodiments, the targeting moiety comprises an antibody, or a functional fragment thereof.

By immunoglobulin" or "antibody" herein is meant a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter. Such antibodies include IgG1, IgG2a, IgG3, IgG4 (and IgG4 subforms), as well as IgA isotypes.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin The terms "full-length antibody", "intact antibody", "and "whole antibody" are used herein interchangeably to refer to an antibody having a structure substantially similar to a native antibody structure or having heavy chains that contain an Fc region as defined herein.

By "native antibodies" herein is meant naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

By "antibody fragment" herein is meant a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), single-domain antibodies, and multispecific antibodies formed from antibody fragments. For a review of certain antibody fragments, see Hudson et al., Nat Med 9, 129-134 (2003). For a review of scFv fragments, see e.g. Pliickthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B 1). Antibody fragments can be made by various techniques, including but not limited to proteolytic digestion of an intact antibody as well as production by recombinant host cells (e.g. *E. coli* or phage), as described herein.

By "antigen binding domain" herein is meant the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

By "variable region" or "variable domain" herein is meant the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

By "hypervariable region" or "HVR" herein is meant each of the regions of an antibody variable domain which are hypervariable in sequence and/or form structurally defined loops "hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The antibody of the present invention can be chimeric antibodies, humanized antibodies, human antibodies, or antibody fusion proteins.

By "chimeric antibody" herein is meant a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a subhuman primate, cat or dog.

By "humanized antibody" herein is meant a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody. In some embodiments, specific residues of the framework region of the humanized antibody, particularly those that are touching or close to the CDR sequences, may be modified, for example replaced with the corresponding residues from the original rodent, subhuman primate, or other antibody.

By "human antibody" herein is meant an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al, Nature Genet. 7: 13 (1994), Lonberg et al, Nature 368:856 (1994), and Taylor et al, Int. Immun 6:579 (1994). A fully human antibody also can be constructed by genetic or chromosomal transfection methods, as well as phage display technology, all of which are known in the art. See for example, McCafferty et al, Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated herein by reference in their entirety.

By "antibody fusion protein" herein is meant a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or mutlivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

In some embodiments, the targeting moiety is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art can be used in the compounds of the invention, in particular for the treatment of the disease with which the target antigen is associated. Examples of target antigens (and their associated diseases) to which an antibody-linker-drug conjugate of the invention can be targeted include: CD2, CD19, CD20, CD22, CD27, CD33, CD37, CD38, CD40, CD44, CD47, CD52, CD56, CD70, CD79, CD137, 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3.

In some embodiments, the antibody is selected from the group consisting of: Rituxan (rituximab), Herceptin (trastuzumab), Erbitux (cetuximab), Vectibix (Panitumumab), Arzerra (Ofatumumab), Benlysta (belimumab), Yervoy (ipilimumab), Perjeta (Pertuzumab), Tremelimumab, Nivolumab, Dacetuzumab, Urelumab, MPDL3280A, Lambrolizumab, and Blinatumomab.

Rituxan (Rituximab) is a chimeric antibody used for the treatment of B-cell non-Hodgkin's lymphoma. It acts on the surface of B cells expressing the CD20 antigen that is expressed on 90% of B-cell non-Hodgkin's lymphoma. Rituxan binds CD20 to induce B cell lysis through CDC and ADCC, as well as sensitize human lymphocytes that are drug resistance for some cytotoxic chemotherapeutics.

Herceptin (Trastuzumab) is a humanized monoclonal antibody that acts on human epidermal growth factor receptor extracellular domain of Her2, which is expressed in 25%-30% of breast cancer. It is believed that Trastuzumab has anti-tumor effect through (1) down-regulation Her2 receptor, inhibition of Her2 intracellular signaling transduction pathways and induction of apoptosis; (2) immune mechanisms related antibody dependent ADCC and CDC to kill tumor cells; (3) enhance the effects of chemotherapy.

Erbitux (Cetuximab) is a chimeric antibody that acts on epidermal growth factor receptor (EGFR). Erbitux binds EGFR to inhibit its signal transduction pathway, affecting cell proliferation, invasion and metastasis, and angiogenesis. Inhibition of EGFR signal transduction pathway can enhance chemotherapy drugs and radiation therapy efficacy.

Avastin (Bevacizumab) is a humanized monoclonal antibody that targets vascular endothelial growth factor (VEGF). Its binding of VEGFR inhibits VEGF and signal transduction, resulting in inhibition of tumor angiogenesis.

Other antibodies that currently under development can also be used as targeting moiety. For example, therapeutic monoclonal antibodies against the following targets are under development for treatment of tumors: CD2, CD19, CD20, CD22, CD27, CD33, CD37, CD38, CD40, CD44, CD47, CD52, CD56, CD70, CD79, and CD137 and the following targets for treatment of tumors: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin αv, Integrin αvβ, KIR, LAG-3, Lewis, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, and VEGFR-3 and their variant. (Scott A M, Wolchok J D, Old L J. Antibody Therapy of Cancer. Nat Rev Cancer. 2012 Mar. 22; 12(4):278-87).

In some embodiments, the targeting moiety comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

The following table shows the various antibody structures and the targets being studied.

TABLE 1

| Antibody Structure | Exemplary Target |
|---|---|
| scFv | CC49, ERBB2, Ley |
| Diabody | Ley and TAG-72 |
| Affibody | ERBB2 |
| Minibody | CEA, ERBB2 |
| Protein-Fc | Angiopoietin 1, angiopoietin 2, VEGFR1, VEGER2 |
| Intact IgG | CD20, CD33, EGFR, ERBB2, VEGF |
| IgE and IgM | GM2 |
| Drug conjugates | CD30, CD33 and ERBB2 |

TABLE 1-continued

| Antibody Structure | Exemplary Target |
|---|---|
| Loaded nanoparticles | A33, EGFR and transferrin. |
| Bispecifics | CD19-CD3, EPCAM---CD3, gp100-CD3 |

In some embodiments, the targeting moiety comprises a ATWLPPR (SEQ ID NO:1) polypeptide of VEGFR, Thrombospondin-1 mimetics, CDCRGDCFCG (cyclic) (SEQ ID NO:2) polypeptide, SCH 221153 fragment, NCNGRC (cyclic) (SEQ ID NO:3) polypeptide, CTTHWGFTLC (SEQ ID NO:4) polypeptide, CGNKRTRGC (SEQ ID NO:5) polypeptide (LyP-1), Octreotide, Vapreotide, Lanreotide, C-3940 polypeptide, Decapeptyl, Lupron, Zoladex, or Cetrorelix.

Folic Acid

In some embodiments, the targeting moiety comprises folic acid or a derivative thereof.

In recent years, research on folic acid had made great progress. Folic acid is a small molecule vitamin that is necessary for cell division. Tumor cells divide abnormally and there is a high expression of folate receptor (FR) on tumor cell surface to capture enough folic acid to support cell division.

Data indicate FR expression in tumor cells is 20-200 times higher than normal cells. The expression rate of FR in various malignant tumors are: 82% in ovarian cancer, 66% in non-small cell lung cancer, 64% in kidney cancer, 34% in colon cancer, and 29% in breast cancer (Xia W, Low P S. Late-targeted therapies for cancer. J Med Chem. 2010; 14; 53 (19):6811-24). The expression rate of FA and the degree of malignancy of epithelial tumor invasion and metastasis is positively correlated. FA enters cell through FR mediated endocytosis, and FA through its carboxyl group forms FA complexes with drugs which enter the cells. Under acidic conditions (pH value of 5), FR separates from the FA, and FA releases drugs into the cytoplasm.

Clinically, the system can be used to deliver drugs selectively attack the tumor cells. Folic acid has small molecular weight, has non-immunogenicity and high stability, and is inexpensive to synthesis. More importantly, chemical coupling between the drug and the carrier is simple, and as such using FA as targeting molecule to construct drug delivery system has become a research hotspot for cancer treatment. Currently EC145 (FA chemotherapy drug conjugate compound) that is in clinical trials can effectively attack cancer cells (Pribble P and Edelman M J. EC145: a novel targeted agent for adenocarcinoma of the lung. Expert Opin. Investig. Drugs (2012) 21:755-761).

Other Targeting Moieties

In some embodiments, the targeting moiety comprises extracellular domains (ECD) or soluble form of PD-1, CTLA4, CD47, BTLA, KIR, TIM3, 4-1BB, and LAG3, full length of partial of a surface ligand Amphiregulin, Betacellulin, EGF, Ephrin, Epigen, Epiregulin, IGF, Neuregulin, TGF, TRAIL, or VEGF.

Nanoparticles

In some embodiments, the targeting moiety comprises a particle (target particle), preferably a nanoparticle, optionally a targeted nanoparticle that attached to a targeting molecule that can binds specifically or preferably to a target. In some embodiments, the targeting particle by itself guides the compound of the present invention (such as by enrichment in tumor cells or tissue) and there is no additional targeting molecules attached therein.

By "nanoparticle" herein is meant any particle having a diameter of less than 1000 nm. In some embodiments, a therapeutic agent and/or targeting molecule can be associated with the polymeric matrix. In some embodiments, the targeting molecule can be covalently associated with the surface of a polymeric matrix. In some embodiments, covalent association is mediated by a linker. In some embodiments, the therapeutic agent can be associated with the surface of, encapsulated within, surrounded by, and/or dispersed throughout the polymeric matrix. U.S. Pat. No. 8,246,968, which is incorporated in its entirety.

In general, nanoparticles of the present invention comprise any type of particle. Any particle can be used in accordance with the present invention. In some embodiments, particles are biodegradable and biocompatible. In general, a biocompatible substance is not toxic to cells. In some embodiments, a substance is considered to be biocompatible if its addition to cells results in less than a certain threshold of cell death. In some embodiments, a substance is considered to be biocompatible if its addition to cells does not induce adverse effects. In general, a biodegradable substance is one that undergoes breakdown under physiological conditions over the course of a therapeutically relevant time period (e.g., weeks, months, or years). In some embodiments, a biodegradable substance is a substance that can be broken down by cellular machinery. In some embodiments, a biodegradable substance is a substance that can be broken down by chemical processes. In some embodiments, a particle is a substance that is both biocompatible and biodegradable. In some embodiments, a particle is a substance that is biocompatible, but not biodegradable. In some embodiments, a particle is a substance that is biodegradable, but not biocompatible.

In some embodiments, particles are greater in size than the renal excretion limit (e.g. particles having diameters of greater than 6 nm). In some embodiments, particles are small enough to avoid clearance of particles from the bloodstream by the liver (e.g. particles having diameters of less than 1000 nm). In general, physiochemical features of particles should allow a targeted particle to circulate longer in plasma by decreasing renal excretion and liver clearance.

It is often desirable to use a population of particles that is relatively uniform in terms of size, shape, and/or composition so that each particle has similar properties. For example, at least 80%, at least 90%, or at least 95% of the particles may have a diameter or greatest dimension that falls within 5%, 10%, or 20% of the average diameter or greatest dimension. In some embodiments, a population of particles may be heterogeneous with respect to size, shape, and/or composition.

Zeta potential is a measurement of surface potential of a particle. In some embodiments, particles have a zeta potential ranging between −50 mV and +50 mV. In some embodiments, particles have a zeta potential ranging between −25 mV and +25 mV. In some embodiments, particles have a zeta potential ranging between −10 mV and +10 mV. In some embodiments, particles have a zeta potential ranging between −5 mV and +5 mV. In some embodiments, particles have a zeta potential ranging between 0 mV and +50 mV. In some embodiments, particles have a zeta potential ranging between 0 mV and +25 mV. In some embodiments, particles have a zeta potential ranging between 0 mV and +10 mV. In some embodiments, particles have a zeta potential ranging between 0 mV and +5 mV. In some embodiments, particles have a zeta potential ranging between −50 mV and 0 mV. In some embodiments, particles have a zeta potential ranging between −25 mV and 0 mV. In some embodiments, particles have a zeta potential ranging between −10 mV and 0 mV. In some embodiments, particles have a zeta potential ranging between −5 mV and 0 mV. In some embodiments, particles have a substantially neutral zeta potential (i.e. approximately 0 mV).

A variety of different particles can be used in accordance with the present invention. In some embodiments, particles are spheres or spheroids. In some embodiments, particles are spheres or spheroids. In some embodiments, particles are flat or plate-shaped. In some embodiments, particles are cubes or cuboids. In some embodiments, particles are ovals or ellipses. In some embodiments, particles are cylinders, cones, or pyramids.

In some embodiments, particles are microparticles (e.g. microspheres). In general, a "microparticle" refers to any particle having a diameter of less than 1000 μm. In some embodiments, particles are picoparticles (e.g. picospheres). In general, a "picoparticle" refers to any particle having a diameter of less than 1 nm. In some embodiments, particles are liposomes. In some embodiments, particles are micelles.

Particles can be solid or hollow and can comprise one or more layers (e.g., nanoshells, nanorings). In some embodiments, each layer has a unique composition and unique properties relative to the other layer(s). For example, particles may have a core/shell structure, wherein the core is one layer and the shell is a second layer. Particles may comprise a plurality of different layers. In some embodiments, one layer may be substantially cross-linked, a second layer is not substantially cross-linked, and so forth. In some embodiments, one, a few, or all of the different layers may comprise one or more therapeutic or diagnostic agents to be delivered. In some embodiments, one layer comprises an agent to be delivered, a second layer does not comprise an agent to be delivered, and so forth. In some embodiments, each individual layer comprises a different agent or set of agents to be delivered.

In some embodiments, a particle is porous, by which is meant that the particle contains holes or channels, which are typically small compared with the size of a particle. For example a particle may be a porous silica particle, e.g., a mesoporous silica nanoparticle or may have a coating of mesoporous silica (Lin et al., 2005, J. Am. Chem. Soc., 17:4570). Particles may have pores ranging from about 1 nm to about 50 nm in diameter, e.g., between about 1 and 20 nm in diameter. Between about 10% and 95% of the volume of a particle may consist of voids within the pores or channels.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other nanoparticles that can be associated with inventive nanoparticles etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties.

Examples of polymers include polyalkylenes (e.g. polyethylenes), polycarbonates (e.g. poly(1,3-dioxan-2one)), polyanhydrides (e.g. poly(sebacic anhydride)), polyhydroxyacids (e.g. poly((3-hydroxyalkanoate)), polyfumarates, polycaprolactones, polyamides (e.g. polycaprolactam), polyacetals, polyethers, polyesters (e.g. polylactide, polyglycolide), poly(orthoesters), polyvinyl alcohols, polyurethanes, polyphosphazenes, polyacrylates, polymethacrylates, polycyanoacrylates, polyureas, polystyrenes, and polyamines. In some embodiments, polymers in accordance with the present invention include polymers which have been approved for use in humans by the U.S. Food and Drug Administration (FDA) under 21 C.F.R. §177.2600, including but not limited to polyesters (e.g. polylactic acid, polyglycolic acid, poly(lactic-co-glycolic acid), polycaprolactone, polyvalerolactone, poly(1,3-dioxan-2one)); polyanhydrides (e.g. poly(sebacic anhydride)); polyethers (e.g., polyethylene glycol); polyurethanes; polymethacrylates; polyacrylates; and polycyanoacrylates.

In some embodiments, particles can be non-polymeric particles (e.g. metal particles, quantum dots, ceramic particles, polymers comprising inorganic materials, bone-derived materials, bone substitutes, viral particles, etc.). In some embodiments, a therapeutic or diagnostic agent to be delivered can be associated with the surface of such a non-polymeric particle. In some embodiments, a non-polymeric particle is an aggregate of non-polymeric components, such as an aggregate of metal atoms (e.g. gold atoms). In some embodiments, a therapeutic or diagnostic agent to be delivered can be associated with the surface of and/or encapsulated within, surrounded by, and/or dispersed throughout an aggregate of non-polymeric components.

Particles (e.g. nanoparticles, microparticles) may be prepared using any method known in the art. For example, particulate formulations can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanoparticles have been described (Pellegrino et al., 2005, Small, 1:48; Murray et al., 2000, Ann. Rev. Mat. Sci., 30:545; and Trindade et al., 2001, Chem. Mat., 13:3843).

Methods for making microparticles for delivery of encapsulated agents are described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6: 275; and Mathiowitz et al., 1988, J. Appl. Polymer Sci., 35:755).

Nucleic Acid Targeting Moieties

In some embodiments, the targeting moiety comprises an nucleic acid targeting moiety.

In general, a nucleic acid targeting moiety is any polynucleotide that binds to a component associated with an organ, tissue, cell, extracellular matrix component, and/or intracellular compartment (the target).

In some embodiments, nucleic acid targeting moieties are aptamers.

An aptamer is typically a polynucleotide that binds to a specific target structure that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

In some embodiments, nucleic acid targeting moieties are spiegelmers (PCT Publications WO 98/08856, WO 02/100442, and WO 06/117217). In general, spiegelmers are synthetic, mirror-image nucleic acids that can specifically bind to a target (i.e. mirror image aptamers). Spiegelmers are characterized by structural features which make them not susceptible to exo- and endo-nucleases.

One of ordinary skill in the art will recognize that any nucleic acid targeting moiety (e.g. aptamer or spiegelmer) that is capable of specifically binding to a target can be used in accordance with the present invention. In some embodiments, nucleic acid targeting moieties to be used in accordance with the present invention may target a marker associated with a disease, disorder, and/or condition. In some embodiments, nucleic acid targeting moieties to be used in accordance with the present invention may target cancer-associated targets. In some embodiments, nucleic acid targeting moieties to be used in accordance with the present invention may target tumor markers. Any type of cancer and/or any tumor marker may be targeted using nucleic acid targeting moieties in accordance with the present invention. To give but a few examples, nucleic acid targeting moieties may target markers associated with prostate cancer, lung cancer, breast cancer, colorectal cancer, bladder cancer, pancreatic cancer, endometrial cancer, ovarian cancer, bone cancer, esophageal cancer, liver cancer, stomach cancer, brain tumors, cutaneous melanoma, and/or leukemia.

Nucleic acids of the present invention (including nucleic acid nucleic acid targeting moieties and/or functional RNAs to be delivered, e.g., RNAi-inducing entities, ribozymes, tRNAs, etc., described in further detail below) may be prepared according to any available technique including, but not limited to chemical synthesis, enzymatic synthesis, enzymatic or chemical cleavage of a longer precursor, etc. Methods of synthesizing RNAs are known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in molecular biology, v. 288 (Clifton, N.J.) Totowa, N.J.: Humana Press, 2005).

The nucleic acid that forms the nucleic acid nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid nucleic acid targeting moiety can be replaced with a hydrocarbon linker or a polyether linker provided that the binding affinity and selectivity of the nucleic acid nucleic acid targeting moiety is not substantially reduced by the substitution (e.g., the dissociation constant of the nucleic acid nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) Antisense Drug Technology: Principles, Strategies, and Applications (1st ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, SR, NH2, NHR, NR2 or CN, wherein R is C1-C6 alkyl, alkenyl, or alkynyl, and halo is F, Cl, Br, or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of a nucleic acid targeting moiety such that the ability of the nucleic acid targeting moiety to specifically bind to the target is not substantially affected. The modified region may be at the 5'-end and/or the 3'-end of one or both strands. For example, modified nucleic acid targeting moieties in which approximately 1-5 residues at the 5' and/or 3' end of either of both strands are nucleotide analogs and/or have a backbone modification have been employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Application Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic or diagnostic agent, improved specific binding of an nucleic acid targeting moiety to a target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the nucleic acid targeting moiety are inverted to yield a linkage such as a 3'-3' linkage or a 5'-5' linkage.

In some embodiments, nucleic acids in accordance with the present invention are not synthetic, but are naturally-occurring entities that have been isolated from their natural environments.

Any method can be used to design novel nucleic acid targeting moieties (see, e.g., U.S. Pat. Nos. 6,716,583; 6,465,189; 6,482,594; 6,458,543; 6,458,539; 6,376,190; 6,344,318; 6,242,246; 6,184,364; 6,001,577; 5,958,691; 5,874,218; 5,853,984; 5,843,732; 5,843,653; 5,817,785; 5,789,163; 5,763,177; 5,696,249; 5,660,985; 5,595,877; 5,567,588; and 5,270,163; and U.S. Patent Application Publications 2005/0069910, 2004/0072234, 2004/0043923, 2003/0087301, 2003/0054360, and 2002/0064780). The present invention provides methods for designing novel nucleic acid targeting moieties. The present invention further provides methods for isolating or identifying novel nucleic acid targeting moieties from a mixture of candidate nucleic acid targeting moieties.

Nucleic acid targeting moieties that bind to a protein, a carbohydrate, a lipid, and/or a nucleic acid can be designed and/or identified. In some embodiments, nucleic acid targeting moieties can be designed and/or identified for use in the complexes of the invention that bind to proteins and/or characteristic portions thereof, such as tumor-markers, integrins, cell surface receptors, transmembrane proteins, intercellular proteins, ion channels, membrane transporter proteins, enzymes, antibodies, chimeric proteins etc. In some embodiments, nucleic acid targeting moieties can be designed and/or identified for use in the complexes of the invention that bind to carbohydrates and/or characteristic portions thereof, such as glycoproteins, sugars (e.g., monosaccharides, disaccharides and polysaccharides), glycocalyx (i.e., the carbohydrate-rich peripheral zone on the outside surface of most eukaryotic cells) etc. In some embodiments, nucleic acid targeting moieties can be designed and/or identified for use in the complexes of the invention that bind to lipids and/or characteristic portions thereof, such as oils, saturated fatty acids, unsaturated fatty acids, glycerides, hormones, steroids (e.g., cholesterol, bile acids), vitamins (e.g. vitamin E), phospholipids, sphingolipids, lipoproteins etc. In some embodiments, nucleic acid targeting moieties can be designed and/or identified for use in the complexes of the invention that bind to nucleic acids and/or characteristic portions thereof, such as DNA nucleic acids; RNA nucleic acids; modified DNA nucleic acids; modified RNA nucleic acids; and nucleic acids that include any combination of DNA, RNA, modified DNA, and modified RNA; etc.

Nucleic acid targeting moieties (e.g. aptamers or spiegelmers) may be designed and/or identified using any available method. In some embodiments, nucleic acid targeting moieties are designed and/or identified by identifying nucleic acid targeting moieties from a candidate mixture of nucleic acids. Systemic Evolution of Ligands by Exponential Enrichment (SELEX), or a variation thereof, is a commonly used method of identifying nucleic acid targeting moieties that bind to a target from a candidate mixture of nucleic acids.

Nucleic acid targeting moieties that bind selectively to any target can be isolated by the SELEX process, or a variation thereof, provided that the target can be used as a target in the SELEX process.

B. Activating Moiety

In general, the compound of the present invention comprises an activating moiety.

By "activating moiety" herein is meant a molecule or agent that is capable of stimulating or enhancing the body's immune system or tumor cells. In general, the activating moiety acts, directly or indirectly, on toll like receptors, nucleotide-oligomerization domain-like receptors, RIG-I-Like receptors, c-type lectin receptors, or cytosolic DNA Sensors, or a combination thereof.

In some embodiments, the activating moiety is capable of activating human immune cells, including but not limited to dendritic cells, macrophages, monocytes, myeloid-derived suppressor cells, NK cells, B cells, T cells, or tumor cells, or a combination thereof.

Dendritic Cells

Dendritic cells are the most powerful antigen-presenting cells. Dendritic cells play an essential role for the initiation of both innate and adaptive immune responses. Dendritic cells also play a key role in the induction and maintenance of immune tolerance.

By "dendritic cells" (DC) herein is meant a heterogeneous cell population including two main subtypes: namely, myeloid DC (mDC) and plasmacytoid DC (pDC) (Steinman et al., 1979, J. Exp. Med., 149, 1-16). These two blood DC subsets were originally differentiated by their expression of CD11c (integrin complement receptor) and CD123 (IL-3Rα). Each of the pDC and mDC populations constitutes between about 0.2 to about 0.6% of the PBMC population in humans.

By "pDC" herein is meant plasmacytoid dendritic cells and they represent a subtype of dendritic cells found in the blood and peripheral lymphoid organs. These cells express the surface markers CD123, BDCA-2(CD303) and BDCA-4(CD304) and HLA-DR, but do not express CD11c, CD14, CD3, CD20 or CD56, which distinguishes them from conventional dendritic cells, monocytes, T-cells, B cells and NK cells. As components of the innate immune system, these cells express intracellular Toll-like receptors 7 and 9, which enable the detection of viral and bacterial nucleic acids, such as ssRNA or CpG DNA motifs. Upon stimulation and subsequent activation, these cells produce large amounts of Type I interferon (mainly IFN-α and IFN-β) and Type III interferon (e.g., IFN-λ), which are critical pleiotropic anti-viral compounds mediating a wide range of effects. By generating a large number of type I interferon, cytokines and chemokines, plasmacytoid dendritic cells are widely involved in the body's innate and adaptive immune responses. They can regulate NK cells, T cells, B cells and other cells involved in immune response intensity, duration, and response mode, thus play a very important function in tumor, infection and autoimmune disease. (Liu Y J. IPC: professional type 1 interferon-producing cells and plasmacytoid dendritic cell precursors. Annu Rev Immunol. 2005; 23:275-306. Gilliet M, Cao W, Liu Y J. Plasmacytoid dendritic cells: sensing nucleic acids in viral infection and autoimmune diseases. Nat Rev Immunol. 2008 August; 8 (8):594-606).

By "mDC" herein is meant myeloid dendritic cells and they represent a subtype of circulating dendritic cells found in blood and peripheral lymphoid organs. These cells express the surface markers CD11c, CD1a, HLA-DR and either BDCA-1 (CD1c) or BDCA-3 (CD141). They do not express BDCA-2 or CD123, which distinguishes them from pDC. mDC also do not express CD3, CD20 or CD56. As components of the innate immune system, mDC express Toll-like receptors (TLR), including TLR2, 3, 4, 5, 6 and 8, which enable the detection of bacterial and viral components. Upon stimulation and subsequent activation, these cells are the most potent antigen presenting cells to activate antigen-specific CD4 as well as CD8 T cells. In addition, mDCs has the ability to produce large amounts of IL-12 and IL23, which is critical for the induction of Th1-mediated or Th17 cell-mediated immunity Study found that many solid tumors such as breast cancer and head and neck cancer, ovarian cancer has pDC's invasion (Treilleux I, Blay J Y, Bendriss-Vermare N et al. Dendritic cell infiltration and prognosis of early stage breast cancer. Clin Cancer Res 2004; 10:7466-7474. Hartmann E, Wollenberg B, Rothenfusser S et al. Identification and functional analysis of tumor-infiltrating plasmacytoid dendritic cells in head and neck cancer. Cancer Res 2003; 63:6478-6487. Zou W P, Machelon V, Coulomb-L'Hermin A, et al. Stromal-derived factor-1 in human tumors recruits and alters the function of plasmacytoid precursor dendritic cells. Nat Med 2001; 7:1339-1346) and factors secreted by tumor cells inhibit DC maturation. (Gabrilovich D I, Corak J, Ciernik I F et al. Decreased antigen presentation by dendritic cells in patients with breast cancer. Clin Cancer Res 1997; 3:483-490. Bell D, Chomarat P, Broyles D et al. In breast carcinoma tissue, immature dendritic cells reside within the tumor, whereas mature dendritic cells are located in peritumoral areas. J Exp Med 1999; 190:1417-1425. Menetrier-Caux C, Montmain G, Dieu M C et al Inhibition of the differentiation of dendritic cells from CD34 (+) progenitors by tumor cells: role of interleukin-6 and macrophage colony-stimulating factor. Blood 1998; 92:4778-4791). These immature DC cells did not play a role in promoting anti-tumor immunity. By contrast, DCs within the tumor microenvironment promote tumor growth by inhibiting antitumor immunity and by promoting angiogenesis. There is evidence that Toll-like receptor 7 agonist Imiquimod, and Toll-like receptor 9 agonist CpG drugs can stimulate pDC within the tumor microenvironment to inhibit tumor development. (Dummer R, Urosevic M, Kempf W et al. Imiquimod in basal cell carcinoma: how does it work? Br J Dermatol 2003; 149:57-58. Miller R L, Gerster J F, Owens M L et al Imiquimod applied topically: a novel immune response modifier and new class of drug. Int J Immunopharmacol 1999; 21:1-14. Hofmann M A, Kors C, Audring H et al Phase 1 evaluation of intralesionally injected TLR9-agonist PF-3512676 in patients with basal cell carcinoma or metastatic melanoma. J Immunother 2008; 31:520-527).

In some embodiments, the human dendritic cell is a plasmacytoid dendritic cell.

In some embodiments, the human dendritic cell is a myeloid dendritic cell.

In some embodiments, the activating moiety is capable of binding specifically to human TLR7 or TLR8 and thus is capable of activating either pDC or mDC.

In some embodiments, the activating moiety is capable of binding specifically to both human TLR7 and TLR8, thus is capable of activating both pDC and mDC. pDCs selectively express endosomal Toll-like receptor (TLR) 7 and TLR9, whereas mDCs selectively express TLR8. Bao M, Liu Y J. Regulation of TLR7/9 signaling in plasmacytoid dendritic cells, Protein Cel. 2013 January; 4(1):40-52. Hémont C, Neel A, Heslan M, Braudeau C, Josien R. Human blood mDC subsets exhibit distinct TLR repertoire and responsiveness. J Leukoc Biol. 2013 April; 93(4):599-609.

Natural Killer Cells (NK Cells)

In some embodiments, the activating moiety is capable of activating natural killer cells (NK cells), preferably human NK cells.

Natural killer (NK) cells are a type of cytotoxic lymphocyte that constitutes a major component of the immune system. NK cells are a subset of peripheral blood lymphocytes defined by the expression of CD56 or CD16 and the absence of the T cell receptor (CD3). They recognize and kill transformed cell lines without priming in an MHC-unrestricted fashion. NK cells play a major role in the rejection of tumors and cells infected by viruses. The process by which an NK cell recognizes a target cell and delivers a sufficient signal to trigger target lysis is determined by an array of inhibitory and activating receptors on the cell surface. NK discrimination of self from altered self involves inhibitory receptor recognition of MHC-I molecules and non-MHC ligands like CD48 and Clr-1b. NK recognition of infected or damaged cells (altered self) is coordinated through stress induced ligands (e.g., MICA, MICB, Rae1, H60, Mult1) or virally encoded ligands (e.g., m157, hemagluttinin) recognized by various activating receptors, including NKG2D, Ly49H and NKp46/Ncr1.

NK cells represent the predominant lymphoid cell in the peripheral blood for many months after allogeneic or autologous stem cell transplant and they have a primary role in immunity to pathogens during this period (Reittie et al (1989) Blood 73: 1351-1358; Lowdell et al (1998) Bone Marrow Transplant 21: 679-686). The role of NK cells in engraftment, graft-versus-host disease, anti-leukemia activity and post-transplant infection is reviewed in Lowdell (2003) Transfusion Medicine 13:399-404.

Human NK cells mediate the lysis of tumor cells and virus-infected cells via natural cytotoxicity and antibody-dependent cellular cytotoxicity (ADCC).

Human NK cells are controlled by positive and negative cytolytic signals. Negative (inhibitory) signals are transduced by C-lectin domain containing receptors CD94/NKG2A and by some Killer Immunoglobulin-like Receptors (KIRs). The regulation of NK lysis by inhibitory signals is known as the "missing self" hypothesis in which specific HLA-class I alleles expressed on the target cell surface ligate inhibitory receptors on NK cells. The down-regulation of HLA molecules on tumor cells and some virally infected cells (e.g. CMV) lowers this inhibition below a target threshold and the target cells may become susceptible to NK cell-mediated lysis if the target cells also carry NK-priming and activating molecules. TLR7, TLR8 or TLR9 agonists can activate both mDC and pDCs to produce type I IFNs and express costimulatory molecules such as GITR-ligand, which subsequently activate NK cells to produce IFN-g and potently promote NK cell killing function.

Inhibitory receptors fall into two groups, those of the Ig-superfamily called Killer Immunoglobulin-like Receptors (KIRs) and those of the lectin family, the NKG2, which form dimers with CD94 at the cell surface. KIRs have a 2- or 3-domain extracellular structure and bind to HLA-A, -B or -C. The NKG2/CD94 complexes ligate HLA-E.

Inhibitory KIRs have up to 4 intracellular domains which contain ITIMs and the best characterized are KIR2DL1, KIR2DL2 and KIR2DL3 which are known to bind HLA-C molecules. KIR2DL2 and KIR2DL3 bind the group 1 HLA-C alleles while KIR2DL1 binds to group 2 alleles. Certain leukemia/lymphoma cells express both group 1 and 2 HLA-C alleles and are known to be resistant to NK-mediated cell lysis With regards to positive activating signals, ADCC is thought to be mediated via CD16, and a number of triggering receptors responsible for natural cytotoxicity have been identified, including CD2, CD38, CD69, NKRP-I, CD40, B7-2, NK-TR, NKp46, NKp30 and NKp44. In addition, several KIR molecules with short intracytoplasmic tails are also stimulatory. These KIRs (KIR2DS1, KIR2DS2 and KIR2DS4) are known to bind to HLA-C; their extracellular domains being identical to their related inhibitory KIRs. The activatory KIRs lack the ITIMs and instead associate with DAP 12 leading to NK cell activation. The mechanism of control of expression of inhibitory versus activatory KIRs remains unknown.

Tumor Cells

In some embodiments, the activating moiety is capable of activating tumor cells. Several reports have described the expression of TLRs in mouse or human cancer or cancer cell lines. For example, TLR1 to TLR6 are expressed by colon, lung, prostate, and melanoma mouse tumor cell lines (Huang B, et al. Toll-like receptors on tumor cells facilitate evasion of immune surveillance. Cancer Res. 2005; 65(12):5009-5014.), TLR3 is expressed in human breast cancer cells (Salaun B, Coste I, Rissoan M C, Lebecque S J, Renno T. TLR3 can directly trigger apoptosis in human cancer cells. J Immunol. 2006; 176(8):4894-4901.), hepatocarcinoma and gastric carcinoma cells express TLR2 and TLR4 (Huang B, et al. *Listeria monocytogenes* promotes tumor growth via tumor cell toll-like receptor 2 signaling. Cancer Res. 2007; 67(9):4346-4352), and TLR9 (Droemann D, et al. Human lung cancer cells express functionally active Toll-like receptor 9. Respir Res. 2005; 6:1.) and TLR4 (He W, Liu Q, Wang L, Chen W, Li N, Cao X. TLR4 signaling promotes immune escape of human lung cancer cells by inducing immunosuppressive cytokines and apoptosis resistance. Mol Immunol 2007; 44(11):2850-2859.) are expressed by human lung cancer cells. TLR7 and TLR8 are found in tumor cells of human lung cancer (Cherfils-Vicini J, Platonova S, Gillard M, Laurans L, Validire P, Caliandro R, Magdeleinat P, Mami-Chouaib F, Dieu-Nosjean M C, Fridman W H, Damotte D, Sautes-Fridman C, Cremer I. J. Clin Invest. 2010; 120(4):1285-1297).

Effect on tumor cells could be various, for instance, stimulation of TLR3 by poly I:C in human breast cancer and melanoma cells directly triggers apoptosis of tumor cells (Salaun B, Coste I, Rissoan M C, Lebecque S J, Renno T. TLR3 can directly trigger apoptosis in human cancer cells. J Immunol. 2006; 176(8):4894-4901., Salaun B, Lebecque S, Matikainen S, Rimoldi D, Romero P. Toll-like receptor 3 expressed by melanoma cells as a target for therapy? Clin Cancer Res. 2007; 13(15 Pt 1):4565-4574.). On the other hand, Human lung cancer cells express functionally active Toll-like receptor 9 and stimulation of the TLR-9 expressing cell lines A549 and HeLa with CpG-ODN showed anti apoptotic effect. Nevertheless, accumulated data shows TLRs are well associated with cancer cells and may effect on it directly or indirectly.

Chemical Composition of Activating Moiety

In general, activating moiety of the present invention comprises a protein, an antibody, a nucleic acid, a small molecule, or a ligand.

In some embodiments, the AM is capable of binding specifically to human TLR7 and/or TLR8.

In some embodiments, the activating moiety comprises: (a) single-stranded RNA (ssRNA), preferably ORN02, ORN06, ssPoly(U), ssRNA40, ssRNA41, ssRNA-DR, or Poly(dT); or (b) a ligand analogs, preferably CL075, CL097, CL264, CL307, Gardiquimod, Loxoribine, Imiquimod, or Resiquimod.

In some embodiments, the activating moiety comprises a TLR ligand (TLRL), a Nod-Like Receptor ligand, a RIG-Like Receptor ligand, a CLR ligand, a CDS ligand, or a inflammasome inducers.

In some embodiments, the activating moiety comprises a ligand of one or more TLRs selected from the group consisting of: TLR2, TLR3, TLR4, TLR5, TLR7, TLR8, TLR7/TLR8, TLR9 and TLR10.

TLR are a family of proteins that sense a microbial product and/or initiates an adaptive immune response. TLRs activate a dendritic cell (DC). TLRs are conserved membrane spanning molecules containing an ectodomain of leucine-rich repeats, a transmembrane domain and an intracellular TIR (Toll/interleukin receptor) domain. TLRs recognize distinct structures in microbes, often referred to as "PAMPs" (pathogen associated molecular patterns). Ligand binding to TLRs invokes a cascade of intracellular signaling pathways that induce the production of factors involved in inflammation and immunity.

Exemplary agonists which may be used for these receptors include, without limitation lipoproteins, lipopolypeptides, peptidoglycans, zymosan, lipopolysaccharide, neisserial porins, flageilin, profiilin, galactoceramide, muramyl dipeptide, giucopyranosyl lipid A (GLA), and resiquimod (R848). Peptidoglycans, lipoproteins, and lipoteichoic acids are cell wall components of Gram-positive. Lipopolysaccharides are expressed by most bacteria. Flageilin is the structural component of bacterial flagella that is secreted by pathogenic and commensal bacterial. A Galactosylceramide (α-GalCer) is an activator of natural killer T (NKT) cells. Muramyl dipeptide is a bioactive peptidoglycan motif common to all bacteria. Such agonists mediate innate immune activation via Toll-like Receptors. Specific binding of an agonist for its cognate receptor is often expressed in terms of an affinity. The ligands of the present invention may bind with affinities of between about $10^4 M^{-1}$ and about $10^8 M^{-1}$. Affinity is calculated as $K_d = k_{off}/k_{on}$, ($k_{off}$ is the dissociation rate constant, $K_{on}$ is the association rate constant and $K_d$ is the equilibrium constant). Single or multiple agonists may be used.

In humans, at least eight TLRs have been identified. TLRs that are expressed on the surface of cells include TLR2, TLR3, TLR4, TLR5, TLR7, TLR8 or TLR7/TLR8, TLR9 and TLR10 are expressed with the ER compartment. Human dendritic cell subsets can be identified on the basis of distinct TLR expression patterns. By way of example, the myeloid or "conventional" subset of DC (mDC) expresses TLRs 2-8 when stimulated, and a cascade of activation markers (e.g.

CD80, CD86, MHC class I and II, CCR7), pro-inflammatory cytokines, and chemokmes are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. Without being bound by any particular theory, as dying tumor cells may adversely affect DC function, it is hypothesized that activating DC with TLR agonists is beneficial for priming anti-tumor immunity in an immunotherapy approach to the treatment of cancer. It has also been suggested that successful treatment of breast cancer using radiation and chemotherapy requires TLR4 activation.

TLR agonists known in the art and useful in the present invention include, but are not limited to, the following: Pam3Cys, a TLR-1/2 agonist; cell-wall components products (LAM, LM, LPS, LTA, LTA), a TLR-2 agonist; MALP2, a TLR-2 agonist; Pam2Cys, a TLR-2 agonist; FSL, a TLR-2 agonist; Zymosan, a TLR-2 agonist; PGN, a TLR-2 agonist; polyribosinic; polyribocytidic acid (Poly I:C), a TLR-3 agonist; polyadenosine-polyuridylie acid (poly AU), a TLR-3 agonist; Polyinosinie-Polycytidylic acid stabilized with poiy-L-lysine and carboxymethylcelitilose (Hilto-nol©), a TLR-3 agonist; monophosphoryl lipid A (MPL), a TLR-4 agonist; LPS, a TLR-4 agonist; bacterial flagellin, a TLR-5 agonist; FLA, a TLR-5 agonist; ORN02, a TLR-7/8 agonist; ORN06, a TLR-7/8 agonist; ssPoly(U), a TLR-7/8 agonist; ssRNA40, a TLR-7/8 agonist; ssRNA41, a TLR-7/8 agonist; ssRNA-DR, a 7/8 agonist; Poly(dT), a TLR-7/8 agonist; CL075, a TLR-7/8 agonist; CL097, a TLR-7/8 agonist; CL264, a TLR-7/8 agonist; CL307, a TLR-7/8 agonist; Gardiquimod, a TLR-7/8 agonist; Loxoribine, a TLR-7/8 agonist; Imiquimod, a TLR-7/8 agonist; Resiquimod a TLR-7/8 agonist; and ODN1585, a TLR-9 agonist; ODN1668, a TLR-9 agonist; ODN1826, a TLR-9 agonist; ODN2006, a TLR-9 agonist; ODN2007, a TLR-9 agonist; ODN2216, a TLR-9 agonist; ODN2336, a TLR-9 agonist; ODN2395, a TLR-9 agonist; ODN M362 a TLR-9 agonist.

In some embodiments, the activating moiety comprises:

(i) a ligand of TLR2 selected from the group consisting of: (a) a heat killed bacteria product, preferably HKAL, HKEB, HKHP, HKLM, HKLP, HKLR, HKMF, HKPA, HKPG, or HKSA, HKSP, and (b) a cell-wall components product, preferably LAM, LM, LPS, LTA, LTA, PGN, FSL, Pam2CSK4, Pam3CSK4, or Zymosan;

(ii) a ligand of TLR3 selected from the group consisting of: Poly (I:C) and Poly (A:U);

(iii) a ligand of TLR4 selected from the group consisting of: LPS and MPLA;

(iv) a ligand of TLR5 selected from the group consisting of: FLA and Flagellin;

(v) a ligand of TLR7, TLR 8, or TLR 7 and TLR, selected from the group consisting of: ORN02 (TLR8), ORN06 (TLR8), ssPoly(U) (TLR8), ssRNA40 (TLR8), ssRNA41 (TLR8), ssRNA-DR (TLR8) Poly(dT) (TLR7/8), CL075 (TLR7/8), CL097 (TLR7/8), CL264 (TLR7), CL307 (TLR7), Gardiquimod (TLR7), Loxoribine (TLR7), Imiquimod (TLR7/8), and Resiquimod (TLR7/8);

(vi) a ligand of TLR9 selected from the group consisting of: ODN1585, ODN1668, ODN1826, ODN2006, ODN2007, ODN2216, ODN2336, ODN2395, and ODN M362;

(vii) a ligand of TLR10;

(viii) a ligand of nucleotide-oligomerization domain (NOD)-like selected from the group consisting of: NOD1 agonist (C12-iE-DAP, iE-DAP, Tri-DAP), NOD2 agonist (L18-MDP, MDP, M-TriLYS, M-TriLYS-D-ASN, Murabutide, N-Glycolyl-MDP), and NOD1/NOD2 agonists (M-TriDAP, PGN);

(ix) a ligand of one or more RIG-I-Like receptors (RLR) selected from the group consisting of: 5'ppp-dsRNA, Poly (dA:dT), Poly(dG:dC), and Poly (I:C);

(x) a ligand of one or more C-type lectin receptors (CLR) selected from the group consisting of: Curdlan AL, HKCA, HKSC, WGP, Zymosan, and Trehalose-6,6-dibehenate;

(xi) a ligand of one or more Cytosolic DNA Sensors (CDS) selected from the group consisting of: c-GMP, c-G-AMP, c-G-GMP, c-A-AMP, c-di-AMP, c-di-IMP, c-di-GMP, c-di-UMP, HSV-60, ISD, pCpG, Poly (dA:dT), Poly(dG:dC), Poly (dA), and VACV-70; and (xii) an inflammasome inducer selected from the group consisting of: (a) NLRP3 inflammasome protein complex, preferably alum Crystals, ATP, CPPD Crystals, Hermozoin, MSU Crystals, Nano-SiO2, Nigericin, and (b) AIM2 inflammasome protein complex, preferably Poly (dA:dT).

In some embodiments, the activating moiety comprises IMO2134, IMO205, MGN-1703, MGN-1704, Agatolimod, SD-101, QAX-935, DIMS0150, Pollinex Quattro, OM-174, Eritoran, TAK-242, NI-0101, Type I interferon, type II interferon, type III interferon, IL-12, IL-23, IL-18, IL-7 or IL-15.

In some embodiments, the activating moiety is capable of binding specifically to human TLR7 and/or TLR8, preferably binds specifically to both TLR7 and TLR8, such as Resiquimod (R848), thus is capable of activating both pDC and mDC. TLR7 and TLR8 are phylogenetically and structurally related. TLR7 is selectively expressed by human pDCs and B cells. TLR8 is predominantly expressed mDCs, monocytes, macrophages and myeloid suppressor cells. TLR7-specific agonists activate plasmacytoid DCs (pDCs) to produce large amounts of type 1 IFNs and expressing high levels of costimulatory molecules that promote activation of T cells, NK cells, B cells and mDCs. TLR8-specific agonists activate myeloid DCs, monocytes, macrophages or myeloid-derived suppressor cells to produce large amounts of type 1 IFN, IL-12 and IL-23, and express high levels of MHC class I, MHC class II and costimulatory molecules that promote the activation of antigen specific CD4 and CD8+ T cells.

Additional moieties or molecules that activate human immune cells through TLR can be identified by TLR reporter cell lines, e.g.: 293/TLR reporter cells from Invi-voGen.

Additional moieties or molecules that can activate TLR7 and/or TLR 8 can be identified using using the 293/TLR reporter cells from InvivoGen, and the ability of these additional moieties to stimulate pDCs to produce type 1 IFN, and to stimulate mDCs to produce type 1 IFN and IL-12, as well as to upregulate the expression of CD80, CD86.

The activating moiety that is capable of activating NK cells via type 1 IFN and co-stimulatory molecules such as GITR-ligand expressed by activated pDC and/or mDC can be identified by NK cell proliferation and expression of activation maker CD69 in total peripheral blood mononuclear cell assay.

The activating moiety that is capable of activating tumor cells to undergo cell death and to produce cytokines such as type 1 IFN, IL-1a/b, TNF or IL-6 can be identified using methods known in the art.

Additional activating moieties or molecules that are capable of activating DC cells, monocytes, macrophages, myeloid suppressor cells, B cells, NK cells, or tumor cells can be identified using methods known in the art.

In some embodiments, when the targeting moiety comprises an antibody (or a fragment thereof), or an aptamer, the activating moiety does not comprise a CpG oligonucleotide.

In some embodiments, specially when the targeting moiety comprises an antibody or a fragment there of, or an aptamer, the activating moiety does not comprise a therapeutic agent, such as chemotherapeutic agents or toxins, such as toxins generally used in antibody-drug conjugates). Thus, in general, the compounds of the present invention do not encompass antibody-drug conjugates (ADC), or antibody-CpG conjugates.

C. Linkers

In general, the compound of the invention comprises a linker that links the targeting moiety and the activating moiety. Though, in some compound there is no linker and the activating moiety and the targeting moiety is linked directly.

By "linker" herein is meant a moiety that connects a first molecule to a second molecule through chemical bonds. In linkers of the invention, the connection can be severed so as to release a biologically active form of the first and/or second molecule. A preferred example of a linker is a moiety that comprises a bond that is stable at neutral pH but is readily cleaved under conditions of low pH. Particularly preferred examples of linkers are moieties that comprise a bond that is stable at pH values between 7 and 8 but is readily cleaved at pH values between 4 and 6. Another example of a linker is a moiety that comprises a bond that is readily cleaved in the presence of an enzyme. Preferred examples of such enzyme-sensitive linkers are peptides comprising a recognition sequence for an endosomal peptidase. Another example of a linker is a redox potential-sensitive linker that is stable under conditions of low reduction potential (e.g., low thiol or glutathione concentration) but cleaved under conditions of high reduction potential (e.g., high thiol or glutathione concentration). Preferred examples of such redox potential-sensitive linkers include disulfides and sulfenamides. Particularly preferred examples include substituted aryl-alkyl disulfides in which the aryl group is substituted with sterically-demanding and electron-withdrawing or electron-donating substitutents, so as to control the sensitivity of the disulfide linkage towards reaction with thiol. Another example of a linker is a moiety that comprises a bond that is readily cleaved upon exposure to radiation. Preferred examples of such radiation-sensitive linkers are 2-nitrobenzyl ethers that are cleaved upon exposure to light. Particularly preferred examples of linkers are moieties that mask the biological activity of one of the two linked molecules until the linkage is severed.

In some embodiments, the compound of the invention comprises a linker that is selected from the group consisting of a hydrazine group, a polypeptide, a disulfide group, and a thioether group.

By "hydrazine group" or "hydrazine linker" or "self-cyclizing hydrazine linker" herein is meant a linker moiety that, upon a change in condition, such as a shift in pH, will undergo a cyclization reaction and form one or more rings. The hydrazine moiety is converted to a hydrazone when attached. This attachment can occur, for example, through a reaction with a ketone group on the L4 moiety. Therefore, the term hydrazine linker can also be used to describe the linker of the current invention because of this conversion to a hydrazone upon attachment.

By "five-membered hydrazine linker" or "5-membered hydrazine linker" herein is meant hydrazine-containing molecular moieties that, upon a change in condition, such as a shift in pH, will undergo a cyclization reaction and form one or more 5-membered rings. Alternatively, this five membered linker may similarly be described as a five-membered hydrazine linker or a 5-membered hydrazine linker.

By "six-membered hydrazine linker" or "6-membered hydrazine linker" herein is meant hydrazine-containing molecular moieties that, upon a change in condition such as a shift in pH, will undergo a cyclization reaction and form one or more 6-membered rings. This six membered linker may similarly be described as a six-membered hydrazine linker or a 6-membered hydrazine linker.

By "cyclization reaction" herein is meant the cyclization of a peptide, hydrazine, or disulfide linker, indicates the cyclization of that linker into a ring and initiates the separation of the drug-ligand complex. This rate can be measured ex situ, and is completed when at least 90%, 95%, or 100% of the product is formed.

In some embodiments, the compound of the present invention comprises a linker region between the targeting moiety and the activating moiety, and the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in targeted cells or tissues. For example, a peptidyl linker that is cleavable by the thiol-dependent protease cathepsin-B, which is highly expressed in cancerous tissue, can be used (e.g., a Phe-Leu or a Gly-Phe-Leu-Gly) linker). Other such linkers are described, e.g., in U.S. Pat. No. 6,214,345. In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In some embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2- pyridyldithio)butyrate) and SMPT (N-succinimidyl-oxycarbonyl-alpha-methyl-alpha-(2-pyridyl-dithio) toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of compounds of the present invention, are cleaved when the compounds of the present invention present in an extracellular environment (e.g., in plasma). Whether a linker is not substantially sensitive to the extracellular environment can be determined, for example, by incubating independently with plasma both (a) the compound of the invention (the "Compound sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the Compound sample with that present in control sample, as measured, for example, by high performance liquid chromatography.

In other, non-mutually exclusive embodiments, the linker promotes cellular internalization. In certain embodiments, the linker promotes cellular internalization when conjugated to the activating moiety. In yet other embodiments, the linker promotes cellular internalization when conjugated to both the targeting moiety and the activating moiety.

A variety of linkers that can be used with the present compositions and methods are described in WO 2004010957 entitled "Drug Conjugates and Their Use for Treating Cancer, An Autoimmune Disease or an Infectious Disease", US20120141509A1, and US20120288512A1 (the disclosure of which is incorporated by reference herein).

In certain embodiments, the linker unit has the following general formula:

-Ta-Ww-Yywherein -T- is a stretcher unit; a is 0 or 1; each —W— is independently an amino acid unit; w is independently an integer ranging from 2 to 12; —Y— is a spacer unit; and y is 0, 1 or 2.

The Stretcher Unit

The stretcher unit (-T-), when present, links the targeting moiety to an amino acid unit (—W—). Useful functional groups that can be present on a targeting moiety, such as an antibody, either naturally or via chemical manipulation include, but are not limited to, sulthydryl, amino, hydroxyl, the anomeric hydroxyl group of a carbohydrate, and carboxyl. Suitable functional groups are sulthydryl and amino. Sulthydryl groups can be generated by reduction of the intramolecular disulfide bonds of an antibody. Alternatively, sulthydryl groups can be generated by reaction of an amino group of a lysine moiety of an antibody with 2-iminothiolane (Traut's reagent) or other sulthydryl generating reagents. In some embodiments, the antibody is a recombinant antibody and is engineered to carry one or more lysines. In other embodiments, the recombinant antibody is engineered to carry additional sulthydryl groups, e.g., additional cysteines.

In some embodiments, the stretcher unit forms a bond with a sulfur atom of the antibody. The sulfur atom can be derived from a sulthydryl (—SH) group of a reduced antibody (A). Representative stretcher units of these embodiments are depicted within the square brackets of Formulas (IIa) and (IIb), wherein A-, —W—, —Y—, -D, w and y are as defined above and $R^1$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)r-, and —($CH_2CH_2O$)r-$CH_2$—; and r is an integer ranging from 1-10.

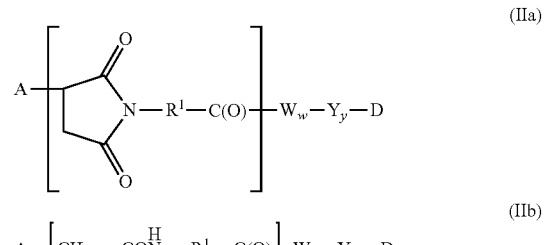

(IIa)

(IIb)

An illustrative stretcher unit is that of formula (IIa) where $R^1$ is —$(CH_2)_5$—:

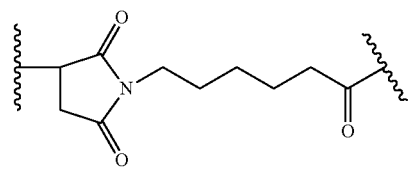

Another illustrative stretcher unit is that of formula (IIa) where $R^1$ is —$(CH_2CH_2O)$r-$CH_2$— and r is 2:

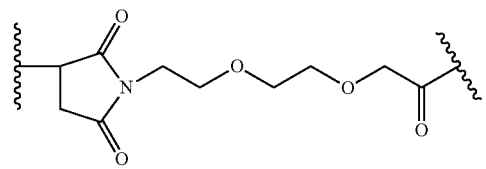

Still another illustrative stretcher unit is that of formula (IIb) where $R^1$ is —$(CH_2)_5$—:

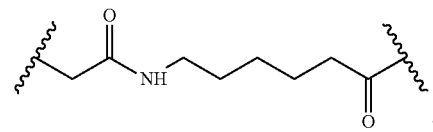

In certain other specific embodiments, the stretcher unit is linked to the antibody unit (A) via a disulfide bond between a sulfur atom of the antibody unit and a sulfur atom of the stretcher unit. A representative stretcher unit of this embodiment is depicted within the square brackets of Formula (III), wherein R¹, A-, —W—, —Y—, -D, w and y are as defined above.

$$A\!\!-\!\![S\!\!-\!\!R^1\!\!-\!\!C(O)]\!\!-\!\!W_w\!\!-\!\!Y_y\text{-}D \quad (III)$$

In other specific embodiments, the reactive group of the stretcher contains a reactive site that can be reactive to an amino group of an antibody. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates. Representative stretcher units of these embodiments are depicted within the square brackets of Formulas (IVa) and (IVb), wherein R¹, A-, —W—, —Y—, -D, w and y are as defined above;

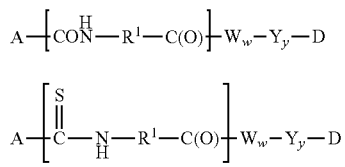

(IVa)

(IVb)

In yet another aspect, the reactive function of the stretcher contains a reactive site that is reactive to a modified carbohydrate group that can be present on an antibody. In some embodiments, the antibody is glycosylated enzymatically to provide a carbohydrate moiety. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, and an arylhydrazide such as those described by Kaneko et al., 1991, Bioconjugate Chem 2:133-41. Representative stretcher units of this embodiment are depicted within the square brackets of Formulas (Va)-(IVc), wherein R¹, A-, —W—, —Y—, -D, w and y are as defined above.

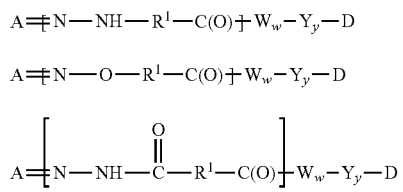

(Va)

(Vb)

(Vc)

The Amino Acid Unit

The amino acid unit (—W—) links the stretcher unit (-T-) to the Spacer unit (—Y—) if the Spacer unit is present, and links the stretcher unit to the cytotoxic or cytostatic agent (Activating Moiety; D) if the spacer unit is absent. -Ww- is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 2 to 12:

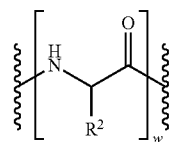

wherein R² is hydrogen, methyl, isopropyl, isobutyl, sec-butyl, benzyl, p-hydroxybenzyl, —CH₂OH, —CH(OH)CH₃, —CH₂CH₂SCH₃, —CH₂CONH₂, —CH₂COOH, —CH₂CH₂CONH₂, —CH₂CH₂COOH, —(CH₂)₃NHC(=NH)NH₂, —(CH₂)₃NH₂, —(CH₂)₃NHCOCH₃, —(CH₂)₃NHCHO, —(CH₂)₄NHC(=NH)NH₂, —(CH₂)₄NH₂, —(CH₂)₄NHCOCH₃, —(CH₂)₄NHCHO, —(CH₂)₃NHCONH₂, —(CH₂)₄NHCONH₂, —CH₂CH₂CH(OH)CH₂NH₂, 2-pyridylmethyl-, 3-pyridylmethyl-, 4-pyridylmethyl-, phenyl, cyclohexyl,

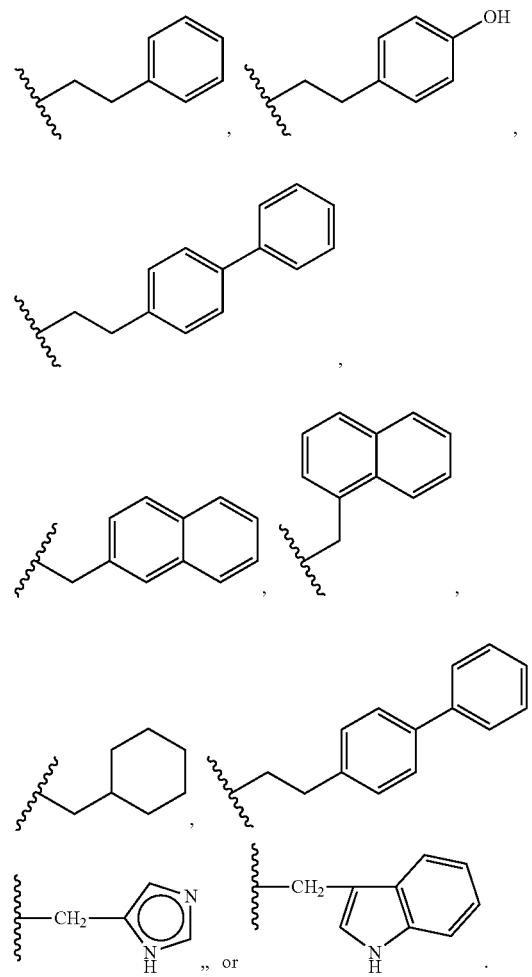

The amino acid unit of the linker unit can be enzymatically cleaved by an enzyme including, but not limited to, a tumor-associated protease to liberate the activating moiety (–D) which is protonated in vivo upon release to provide an activating molecule (D).

Illustrative $W_w$ units are represented by formulas (VI)-(VIII):

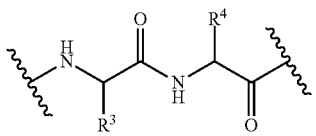

(VI)

wherein $R^3$ and $R^4$ are as follows:

| $R^3$ | $R^4$ |
|---|---|
| Benzyl | $(CH_2)_4NH_2$; |
| Methyl | $(CH_2)_4NH_2$; |
| Isopropyl | $(CH_2)_4NH_2$; |
| Isopropyl | $(CH_2)_3NHCONH_2$; |
| Benzyl | $(CH_2)_3NHCONH_2$; |
| Isobutyl | $(CH_2)_3NHCONH_2$; |
| sec-butyl | $(CH_2)_3NHCONH_2$; |
| —CH$_2$—indole | $(CH_2)_3NHCONH_2$; |
| Benzyl | methyl; and |
| Benzyl | $(CH_2)_3NHC(=NH)NH_2$; |

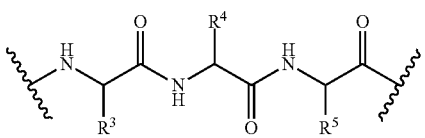

(VII)

wherein $R^3$, $R^4$ and $R^5$ are as follows:

| $R^3$ | $R^4$ | $R^5$ |
|---|---|---|
| Benzyl | benzyl | $(CH_2)_4NH_2$; |
| Isopropyl | benzyl | $(CH_2)_4NH_2$; and |
| H | benzyl | $(CH_2)_4NH_2$; |

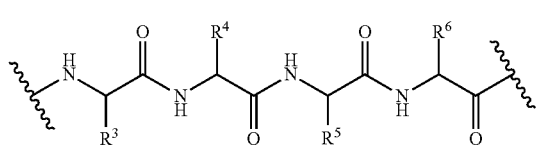

(VIII)

wherein $R^3$, $R^4$, $R^5$ and $R^6$ are as follows:

| $R^3$ | $R^4$ | $R^5$ | $R^6$ |
|---|---|---|---|
| H | Benzyl | isobutyl | H; and |
| methyl | Isobutyl | methyl | isobutyl. |

Suitable amino acid units include, but are not limited to, units of formula (VI) where: $R^3$ is benzyl and $R^4$ is —$(CH_2)_4NH_2$; $R_3$ is isopropyl and $R^4$ is —$(CH_2)_4NH_2$; or $R^3$ is isopropyl and $R^4$ is —$(CH_2)_3NHCONH_2$. Another suitable amino acid unit is a unit of formula (VII), where: $R^3$ is benzyl, $R^4$ is benzyl, and $R^5$ is —$(CH_2)_4NH_2$. -Ww-units can be designed and optimized in their selectivity for enzymatic cleavage by a particular tumor-associated protease. The suitable -Ww- units are those whose cleavage is catalyzed by the proteases, cathepsin B, C and D, and plasmin.

In some embodiments, -Ww- is a dipeptide, tripeptide or tetrapeptide unit.

Where $R^2$, $R^3$, $R^4$, $R^5$ or $R^6$ is other than hydrogen, the carbon atom to which $R^2$, $R^3$, $R^4$, $R^5$ or $R^6$ is attached is chiral. Each carbon atom to which $R^2$, $R^3$, $R^4$, $R^5$ or $R^6$ is attached is independently in the (S) or (R) configuration.

In some embodiments, the amino acid unit is a phenylalanine-lysine dipeptide (Phe-Lys or FK linker). In some embodiments, the amino acid unit is a valine-citrulline dipeptide (Val-Cit or VC linker). In some embodiments, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine, or isonepecotic acid.

The amino acid unit can comprise natural amino acids. In other embodiments, the Amino Acid unit can comprise non-natural amino acids.

The Spacer Unit

The spacer unit (—Y—), when present, links an amino acid unit to the drug unit. Spacer units are of two general types: self-immolative and non self-immolative. A non self-immolative spacer unit is one in which part or all of the spacer unit remains bound to the activating moiety unit after enzymatic cleavage of an amino acid unit from the TM-linker-AM conjugate or the drug-linker compound. Examples of a non self-immolative spacer unit include, but are not limited to a (glycine-glycine) spacer unit and a glycine spacer unit. When a TM-linker-AM conjugate containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from A-T-Ww-. To liberate the AM, an independent hydrolysis reaction should take place within the target cell to cleave the glycine-drug unit bond.

In a typical embodiment, -Yy- is a p-aminobenzyl ether which can be substituted with Qm where Q is —$C_1$-$C_8$ alkyl, —$C1$-$C_8$alkoxy, -halogen, -nitro or -cyano; and m is an integer ranging from 0-4.

In some embodiments, a non self-immolative spacer unit (—Y—) is -Gly-Gly-.

In some embodiments, a non self-immolative the spacer unit (—Y—) is -Gly-.

In one embodiment, the AM-linker compound or an TM-linker-AM conjugate lacks a spacer unit (y=0).

Alternatively, an TM-linker-AM conjugate containing a self-immolative spacer unit can release the AM (D) without the need for a separate hydrolysis step. In these embodiments, —Y— is a p-aminobenzyl alcohol (PAB) unit that is linked to -Ww- via the nitrogen atom of the PAB group, and connected directly to -D via a carbonate, carbamate or ether group.

Other examples of self-immolative spacers include, but are not limited to, aromatic compounds that are electronically equivalent to the PAB group such as 2-aminoimidazol-5-methanol derivatives (see Hay et al., 1999, Bioorg. Med. Chem. Lett. 9:2237 for examples) and ortho or para-aminobenzylacetals. Spacers can be used that undergo facile cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867) Elimination of amine-containing drugs that are substituted at the α-position of glycine (Kingsbury, et al., 1984, J. Med. Chem. 27:1447) are also examples of self-immolative spacer strategies that can be applied to the TM-linker-AM conjugates.

In an alternate embodiment, the spacer unit is a branched bis(hydroxymethyl)styrene (BHMS) unit, which can be used to incorporate moieties.

Typical spacer units (—Yy-) are represented by Formulas (IX)-(XI):

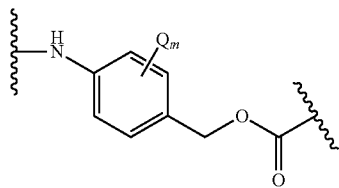

(IX)

where Q is $C_1$-$C_8$ alkyl, $C_1$-$C_8$ alkoxy, halogen, nitro or cyano; and m is an integer ranging from 0-4;

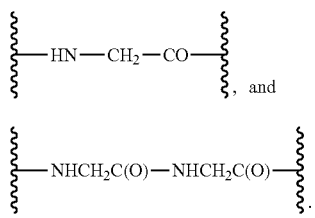

(X)

, and (XI)

In some embodiments, the linker is enzymatic cleavable. In some embodiments, the linker is not enzymatic cleavable.

III. PHARMACEUTICAL FORMULATIONS AND ADMINISTRATION

The present invention further relates to a pharmaceutical formulation comprising a compound of the invention or a pharmaceutically acceptable salt thereof, and one or more pharmaceutically acceptable carriers.

The compounds described herein including pharmaceutically acceptable carriers such as addition salts or hydrates thereof, can be delivered to a patient using a wide variety of routes or modes of administration. Suitable routes of administration include, but inhalation, transdermal, oral, rectal, transmucosal, intestinal and parenteral administration, including intramuscular, subcutaneous and intravenous injections. Preferably, the compounds of the invention comprising an antibody or antibody fragment as the targeting moiety are administered parenterally, more preferably intravenously.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); Ca+2 antagonists (e.g., verapamil, nifedipine, nitrendipine and caroverine); amphotericin; tri-paranol analogues (e.g., tamoxifen); antiarrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, and suspensions for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include calcium carbonate, calcium phosate, various sugars, starches, cellulose derivatives, gelatin, and polymers such as polyethylene glycols.

A preferred pharmaceutical composition is a composition formulated for injection such as intravenous injection and includes about 0.01% to about 100% by weight of the compound of the present invention, based upon 100% weight of total pharmaceutical composition. The drug-ligand conjugate may be an antibody-cytotoxin conjugate where the antibody has been selected to target a particular cancer.

In some embodiments, the pharmaceutical composition of the present invention further comprises a second chemotherapeutic agent.

By "chemotherapeutic agent" herein is meant a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin.

In some embodiments, the second chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

IV. KITS

In another aspect, the present invention provides kits containing one or more of the compounds or compositions of the invention and directions for using the compound or composition. In an exemplary embodiment, the invention provides a kit for conjugating a linker arm of the invention to another molecule. The kit includes the linker, and directions for attaching the linker to a particular functional group. The kit may also include one or more of a cytotoxic drug, a targeting agent, a detectable label, pharmaceutical salts or buffers. The kit may also include a container and optionally one or more vial, test tube, flask, bottle, or syringe. Other formats for kits will be apparent to those of skill in the art and are within the scope of the present invention.

V. MEDICAL USE

In another aspect, the present invention provides a method for treating a disease condition in a subject that is in need of such treatment, comprising: administering to the subject a pharmaceutical composition comprising a therapeutically effective amount of the compound of the present invention a pharmaceutically acceptable salt thereof, and a pharmaceutical acceptable carrier.

In addition to the compositions and constructs described above, the present invention also provides a number of uses of the compounds of the invention. Uses of the compounds of the current invention include: killing or inhibiting the growth or replication of a tumor cell or cancer cell, treating cancer, treating a pre-cancerous condition, preventing the multiplication of a tumor cell or cancer cell, preventing cancer, preventing the multiplication of a cell that expresses an auto-immune antibody. These uses comprise administering to an animal such as a mammal or a human in need thereof an effective amount of a compound of the present invention.

The compound of the current invention is useful for treating diseases such as cancer in an animal, such as a human being. Compositions and uses for treating tumors by providing a subject the composition in a pharmaceutically acceptable manner, with a pharmaceutically effective amount of a composition of the present invention are provided.

By "cancer" herein is meant the pathological condition in humans that is characterized by unregulated cell proliferation. Examples include but are not limited to: carcinoma, lymphoma, blastoma, and leukemia. More particular examples of cancers include but are not limited to: lung (small cell and non-small cell), breast, prostate, carcinoid, bladder, gastric, pancreatic, liver (hepatocellular), hepatoblastoma, colorectal, head and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML).

By "inhibiting" or "treating" or "treatment" herein is meant to reduction, therapeutic treatment and prophylactic or preventative treatment, wherein the objective is to reduce or prevent the aimed pathologic disorder or condition. In one example, following administering of a compound of the present invention, a cancer patient may experience a reduction in tumor size. "Treatment" or "treating" includes (1) inhibiting a disease in a subject experiencing or displaying the pathology or symptoms of the disease, (2) ameliorating a disease in a subject that is experiencing or displaying the pathology or symptoms of the disease, and/or (3) affecting any measurable decrease in a disease in a subject or patient that is experiencing or displaying the pathology or symptoms of the disease. To the extent a compound of the present invention may prevent growth and/or kill cancer cells, it may be cytostatic and/or cytotoxic.

By "therapeutically effective amount" herein is meant an amount of a compound provided herein effective to "treat" a disorder in a subject or mammal. In the case of cancer, the therapeutically effective amount of the drug may either reduce the number of cancer cells, reduce the tumor size, inhibit cancer cell infiltration into peripheral organs, inhibit tumor metastasis, inhibit tumor growth to certain extent, and/or relieve one or more of the symptoms associated with the cancer to some extent.

Administration "in combination with" one or more further therapeutic agents includes simultaneous (concurrent) and consecutive administration in any order. As used herein, the term "pharmaceutical combination" refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

In some embodiments, the diseases condition is tumor.

In some embodiments, the disease condition comprises abnormal cell proliferation, such as a pre-cancerous lesion.

The current invention is particularly useful for the treatment of cancer and for the inhibition of the multiplication of a tumor cell or cancer cell in an animal. Cancer, or a precancerous condition, includes a tumor, metastasis, or any disease or disorder characterized by uncontrolled cell growth, can be treated or prevented by administration the drug-ligand complex of the current invention. The compound delivers the activating moiety to a tumor cell or cancer cell. In some embodiments, the targeting moiety specifically binds to or associates with a cancer-cell or a tumor-cell-associated antigen. Because of its close proximity to the ligand, after being internalized, the activating moiety can be taken up inside a tumor cell or cancer cell through, for example, receptor-mediated endocytosis. The antigen can be attached to a tumor cell or cancer cell or can be an extracellular matrix protein associated with the tumor cell or cancer cell. Once inside the cell, the linker is hydrolytically or enzymatically cleaved by a tumor-cell or cancer-cell-associated proteases, thereby releasing the activating moiety. The released activating moiety is then free to diffuse and induce or enhance immune activity of immune cells or tumor cells. In an alternative embodiment, the activating moiety is cleaved from the compound tumor microenvironment, and the drug subsequently penetrates the cell.

Representative examples of precancerous conditions that may be targeted by the compounds of the present invention, include: metaplasia, hyperplysia, dysplasia, colorectal polyps, actinic ketatosis, actinic cheilitis, human papillomaviruses, leukoplakia, lychen planus and Bowen's disease.

Representative examples of cancers or tumors that may be targeted by compounds of the present invention include: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemia. It will be readily apparent to the ordinarily skilled artisan that the particular targeting moiety used in the compound can be chosen such that it targets the activating moiety to the tumor tissue to be treated with the drug (i.e., a targeting agent specific for a tumor-specific antigen is chosen). Examples of such targeting moiety are well known in the art, examples of which include anti-Her2 for treatment of breast cancer, anti-CD20 for treatment of lymphoma, anti-PSMA for treatment of prostate cancer and anti-CD30 for treatment of lymphomas, including non-Hodgkin's lymphoma.

In some embodiments, the abnormal proliferation is of cancer cells.

In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

In some embodiments, the present invention provides a compound for use in killing a cell. The compound is administered to the cell in an amount sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 30%, 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug). Preferably, the antibody with drug conjugates retards growth of the tumor when administered in the daily dosage amount over a period of at least five days.

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The present invention is further exemplified, but not limited, by the following and Examples that illustrate the preparation of the compounds of the invention.

Example 1

Generation of her2 or egfr Transfected L Cell Lines

Reagents: L cell was from ATCC (Manassas, Va.; Cat No CRL2648), Her2/pEZ-Lv105 or egfr/pCMV cDNA was purchased from Sino Biological Inc., (Cat No H10004) or GeneCopoeia, (Cat No Z2866), Glucose DMEM, L-glutamine, Lipofectamine 2000 (Invitrogen; Carlsbad, Calif.).

To make cell lines for screening the conjugated Trastuzumab, L cell expressing the tagged Her2 or EGFR were generated. The Her2/pEZ-Lv105 or egfr/pCMV cDNA construct was transfected into L cells (that grown in high glucose DMEM+10% FBS+2 mM L-glutamine cells) by the standard Lipofectamine 2000 protocol.

Binding Analysis (FACS Analysis)

To determine binding capability of conjugated Trastuzumab, FACS analysis of L cells expressing human her2 were performance. Briefly, approximately $10^6$ cells of L cells with transient transfected her2 in 100 µl were incubated with varying amounts of Trastuzumab conjugated antibody, PBS or secondary antibody alone or irrelevant huIgG were used as a negative control. After washing, cells were re-suspended in FACS buffer and incubated 30 min at room temperature with 20 µL mouse anti-human IgG conjugated to phycoerythrin (Mu anti-Human-PE) secondary antibody in a 100 µL reaction volume. After washing, cells were fixed in 200 µL of 2% paraformaldehyde/PBS and flow cytometery performed. The same procedure was used for irrelevant human IgG antibody as an isotype control to set baseline PMT per cell line. Flow cytomery was performed on a BD FACSCalibur® and geometric mean fluorescence intensity was recorded for each sample. Recorded data was analyzed using FlowJo software. Results are shown in FIG. 1.

Generation of Antibody with Toll Like Receptor Ligand Conjugates

Reagents: Trastuzumab (Roche/Genentech Corporation, South San Francisco, Calif.), Cetuximab (Merck,); MC-val-cit-PAB linked with resiquimod (MC-vc-PAB-TLRL) or MC-linked with resiquimod (MC-TLRL) (Synthesized in Contract Research Organization, China), Sodium borate, Sodium chloride, Dithiothreitol (DTT), Sephadex G25, DTPA, DTNB, and Maleimidocaproyl-monomethyl (Sigma-Aldrich, Milwaukee, Wis.).

The drugs used for generation of antibody TLR ligand conjugates included Trastuzumab and resiquimod (TLRL), in some case, Cetuximab was used for conjugates. The linkers used for generation of the TLAC were cleavable linker MC-vc-PAB or non cleavable linker MC.

Preparation of Trastuzumab MC-TLRL or Cetuximab MC-TLRL

Trastuzumab was purified from HERCEPTIN® by buffer-exchange at 20 mg/mL, and antibody dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Sigma-Aldrich, Milwaukee, Wis.) and determination of the absorbance at 412 nm. The reduced antibody dissolved in PBS is chilled on ice. The drug linker reagent, Mc-linked with resiquimod, dissolved in DMSO, is diluted in acetonitrile and water at known concentration, and added to the chilled reduced antibody in PBS. After about one hour, an excess of maleimide is added to quench the reaction and cap any unreacted antibody thiol groups. In some case, coupling to lysines of immunoglobulin with standard procedure was performed. The reaction mixture is concentrated by centrifugal ultrafiltration and conjugated antibody is purified and desalted by elution through G25 resin in PBS, filtered through 0.2 nm filters under sterile conditions, and frozen for storage. Preparation of Cetuximab MC-TLRL used the same procedure.

Preparation of Trastuzumab MC-vc-TLRL or Cetuximab MC-vc-TLRL

Antibodies were linked to TLRL through the cysteine by Maleimidocaproyl-valine-citruline (vc)-p-aminobenzyloxycarbonyl (MC-vc-PAB). The MC-vc-PAB linker is cleavable by intercellular proteases such as cathepsin B and when cleaved, releases free drug (Doronina et al., Nat. Biotechnol., 21: 778-784 (2003)) while the MC linker is resistant to cleavage by intracellular proteases. Purified Trastuzumab was dissolved in 500 mM sodium borate and 500 mM sodium chloride at pH 8.0 and further treated with an excess of 100 MM dithiothreitol (DTT). After incubation at 37° C. for about 30 minutes, the buffer is exchanged by elution over Sephadex G25 resin and eluted with PBS with 1 mM DTPA. The thiol/Ab value was checked by determining the reduced antibody concentration from the absorbance at 280 nm of the solution and the thiol concentration by reaction with DTNB (Sigma-Aldrich, Milwaukee, Wis.) and determination of the absorbance at 412 nm (extinction coefficient=13600 cm$^{-1}$ M$^{-1}$). The reduced antibody dissolved in PBS was chilled on ice. The MC-val-cit-PAB-PNP linked with resiquimod in DMSO, was dissolved in acetonitrile and water, and added to the chilled reduced antibody in PBS. After one hour incubation, an excess of maleimide was added to quench the reaction and cap any unreacted antibody thiol groups. In some case, coupling to lysines of immunoglobulin with standard procedure was performed. The reaction mixture was concentrated by centrifugal ultrafiltration and the antibody drug conjugate, was purified and desalted by elution through G25 resin in PBS, filtered through 0.2 µm filters under sterile conditions, and frozen for storage. Preparation of Cetuximab MC-vc-TLRL was the same procedure.

Typically a conjugation reaction of antibody with MC-TLRL or MC-vc-TLRL results in a heterogeneous mixture comprising antibodies different numbers of attached, conjugated TLRL drugs, i.e. drug loading where drug is a distribution from 1 to about 8. Thus, antibody MC-TLRL, or antibody MC-vc-TLRL, includes isolated, purified species molecules as well as mixtures of average drug loading from 1 to 8. By control process, drug loads were in the range of 3-5. The average number of TLRL drug moieties per antibody antibody in compound preparations from conjugation reactions may be characterized by conventional means such as mass spectroscopy, ELISA assay, electrophoresis, and HPLC. The quantitative distribution of antibody MC-TLRL or antibody MC-vc-TLRL in terms of drug may also be determined By ELISA, the averaged value of drug payload number in a particular preparation of antibody with TLRL conjugation may be determined (Hamblett et al (2004) Clinical Cancer Res. 10:7063-7070; Sanderson et al (2005) Clinical Cancer Res. 11:843-852). However, the distribution of drug values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous Trastuzumab MC-TLRL or Trastuzumab MC-vc-TLRL where drug is a certain value from Trastuzumab MC-TLRL or Trastuzumab MC-vc-TLRL with other drug loadings may be achieved by means such as reverse phase HPLC or electrophoresis.

Antibody-Dependent Cell-Mediated Cytotoxicity Assay (ADCC)

Reagents: SKBR3 cells (ATCC, catalog #HTB-30), McCoy's 5A (Invitrogen, Cat No. 22400, Lot No. 747809); RPMI-1640 (Invitrogen, Cat No. 11835, Lot No. 764956); FCS (Hyclone, Cat No. SH30084.03, Lot No. GRH0054); Ficoll-Hypaque (Amersham Biosciences, Piscataway, N.J.; Cat No 17-1440-02), 96 well plate (Costar, Cat No. 3599, Cat No. 3916); Trypan blue (Invitrogen Cat No 15250-061);

LDH kit (Promega, Cat No. G7891), ELISA reader MD5 (Molecule device), Humanized antibody Herceptin® (Genentech Corporation, South San Francisco, Calif.; trade name Trastuzumab) was reconstituted with water to make a 10 mg/ml stock solution before use.

To determine if Trastuzumab conjugated with a high payload of TLRL would still have effector function, antibody-dependent cell-mediated cytotoxicity (ADCC) activities of the several different form of conjugation were tested and compared with the ADCC activity of Trastuzumab reference material which has been shown to have significantly enhanced ADCC activity. ADCC assays were carried out using peripheral blood mononuclear cells (PBMCs) from healthy donors as effector cells, and a human SKBR3 cell line as target cells. On first day, $1 \times 10^4/100$ uL of SKBR3 cells was seeded into the 96 well plates followed by incubation at 37° C. with 5% CO2 for 48 hours.

On third days, human PBMC was prepared fresh from human blood obtained from healthy volunteer donors. Human venous blood samples were collected in ammonium citrate (ACD-A) tubes. The tubes were inverted several times, and whole blood was transferred into one 50 ml conical tube. Blood was diluted 1:3 with PBS in 2% FBS. Ficoll-Hypaque was dispensed slowly underneath blood/PBS mixture. Samples were centrifuged at room temperature at 2400 rpm for 30 minutes before removing the upper layer (plasma/PBS) by aspiration. Buffy coats were collected with sterile pipettes and pooled into a 50 ml conical tube. If visible clumps of WBC remained below the buffy coat, all of the WBC material was collected, with care not to remove excess Ficoll-Hypaque. Sterile PBS-2% FBS was added and mixed by inversion. The diluted PBMC suspensions was centrifuged at 250×g at room temp for 20 minutes, and the cell pellet was collected. The PBMC pellet was suspended in RPMI-1640 medium with 2% heat-inactivated FBS, washed and the number of viable cells was checked by Trypan blue exclusion. $1.2 \times 10^7$ cells/mL in density were prepared and ready to be used. Meanwhile the final concentrations of antibodies the ranged from 12, 4, 1.2, 0.4, 0.12, 0.04, 0.012, 0.004, to 0 μg/mL were well prepared in RPMI-1640.

Serial dilutions of test and control antibodies then were added to wells containing the target cells, PBMC effector cells in 50 μL of RPMI-1640 medium were added to each well with effector:target cell ratio of 60:1 and incubated for an additional 17 hours. The plates were centrifuged at the end of incubation and the supernatants were assayed for lactate dehydrogenase (LDH) activity using a LDH measuring kit. Cell lysis was quantified through absorbance at 490 nm using a microplate reader. The absorbance of wells containing only the target cells served as the control for background, whereas wells containing target cells lysed with Triton-X100 provided maximum signal available. Antibody-independent cellular cytotoxicity was measured in wells containing target and effector cells without the addition of antibody. Cytotoxicity was calculated according to the following equation:

% Cytotoxicity=100%×[$A$490 nm (Sample)–$A$490 (target cell)–$A$490(effect cells]/[$A$490 nm (Target cells lysed)–$A$490 nm (target cells)]

The mean ADCC values from duplicates of sample dilutions were plotted against the antibody concentration, and the EC50 values and the maximum extent of ADCC (%) were generated by fitting into Prism 5 (GraphPad).

Enrichment of Human Dendritic Cells (DCs) from PBMC

Human PBMC was prepared from Buffy coats obtained from healthy volunteer donors by Ficoll centrifugation. Dendritic cells were enriched by using negative depletion with magnetic beads (Miltenyi Biotec) with mixture of anti-CD3, CD19, CD20, CD14, and CD16 antibodies from human PBMC. The enrichment of DCs was stained with goat anti-mouse FITC (lineages), HLA-DR-APCCy7, CD123-BV421 and CD11C-APC. The stained cells were analyzed on BD LSR Fortessa. The anti-CD3, CD4, CD11C, CD19, CD14, CD16, CD123 monoclonal antibody were purchased from BD Biosciences or Biolgend.

FIG. 3($a$) shows the percentages of DCs before and post enrichment. The numbers in upper two plots represent the percentages of DCs (HLA-DR+Lin–) of total cells before and after lineage depletion. The numbers in lower plots represent percentages of mDC (CD11C+CD123–) and pDC (CD123+CD11C–) of total DCs before and after lineage depletion.

Stimulation of Enriched Human DCs and Cytokines Expression $1-2 \times 10^5$ enriched DCs were plated in a 96-well plate in 100 μl media, 100 μl diluted stimulators were add to the plate and cultured for 20-22 h in 37° C. incubator. The supernatant were collected and human IFN-α, IL-6, IL-12(p70) and TNF-α were analyzed by ELISA (Mabtech AB).

Statistical Analysis

The significance of all comparisons was calculated using a Student's two-tailed t test assuming unequal variance between mock and sample groups, and results considered significant when p<0.05. Correlations between parameters were assessed using Spearman's rank correlation test, P values<0.05 were consider to be statistically significant.

In Vivo Tumor Cell Killing Assay Using Trastuzumab TLRL Conjugates or Cetuximab TLRL Conjugates For development of patient-derived gastric carcinoma xenograft (PDX) mouse models, female Balb/c nude mice (from SLAC, Shanghai, China) of 6-8 weeks old were used for tumor fragment implantation. Animals were fed with normal nude mice diet and housed in SPF animal facility in accordance with the Guide for Care and Use of Laboratory Animals and regulations of the Institutional Animal Care and Use Committee. Patent STO#69 gastric tumor fragments of about 15-30 mm$^3$ in size were implanted (s.c.) into right flanks of Balb/c nude mice.

For development of lung cancer xenograft models, Female Balb/c nude mice of 6-8 weeks old were used for tumor fragment implantation. Human lung cancer cell line H1650 (ATCC, Cat. # CRL5883) were cultured in RPMI-1640 medium containing 10% serum, and implanted (s.c.) into right flanks of Balb/c nude mice. Each mouse received $2 \times 10^6$ cells per inoculation in 100 μl of matrigel.

Drugs were administered by i.v. route with 5~20 mg/kg of antibody or 20 mg/kg of Tarceva or reference drug, QWKx3. Tumors were measured once a week by caliper to determine its subcutaneous growth. Tumors were measured twice a week in two dimensions with calipers. Tumor volume was calculated using following formula: tumor volume=(length×width2)×0.5. Average tumor volumes or body weights were plotted using graph program Prism 5 (GraphPad). An endpoint for efficacy study was set at 30-45 days post-first treatment or when a tumor size reached above 2000 mm3, whichever came first. If a mouse lose more than 20% of body weight or is very sick and cannot get to adequate food or water, it will be removed from the study and euthanized. Tumors were collected from mice at the end point, half frozen in LN$_2$ and half fixed in formalin for preparing FFPE tissues.

What is claimed is:

1. A compound having the structure of Formula (I):

TM-$Ln$-AM     (I), wherein TM is a targeting moiety comprising an antibody, or functional fragment thereof, that is capable of binding to a tumor antigen specifically or preferably in comparison to a non-tumor antigen, wherein the tumor antigen is PD-L1;

AM is an activating moiety that is resiquimod, Ln is a linker wherein L has the following formula:

-$T_a$-$W_w$-$Y_y$- wherein

1) T is a stretcher unit, a is 0 or 1, 2) each W is independently an amino acid unit, w is independently an integer of 2 to 12, 3) Y is a spacer unit and a) y is 1, or 2 and Y is self-immolative when a is 0, or b) y is 0, 1, or 2 when a is 1; and 4) n is 1.

2. The compound of claim 1, wherein said the tumor cell is of a carcinoma, a sarcoma, a lymphoma, a myeloma, or a central nervous system cancer.

3. The compound of claim 1, wherein said antibody is MPDL3280A.

4. The compound of claim 1, wherein said antibody or functional fragment thereof comprises a Fab, Fab', F(ab')$_2$, single domain antibody, T and Abs dimer, Fv, scFv, dsFv, ds-scFv, Fd, linear antibody, minibody, diabody, bispecific antibody fragment, bibody, tribody, sc-diabody, kappa (lambda) body, BiTE, DVD-Ig, SIP, SMIP, DART, or an antibody analogue comprising one or more CDRs.

5. The compound of claim 1, wherein said linker is enzymatically cleavable.

6. The compound of claim 1, wherein said linker is not enzymatically cleavable.

7. A pharmaceutical composition comprising a compound as claimed in claim 1, or a pharmaceutically acceptable salt thereof, and one or more pharmaceutically acceptable carriers.

8. The pharmaceutical composition of claim 7, further comprising a second chemotherapeutic agent.

9. The pharmaceutical composition of claim 8, wherein said chemotherapeutic agent is selected from the group consisting of tamoxifen, raloxifene, anastrozole, exemestane, letrozole, imatanib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

* * * * *